United States Patent
Cho et al.

(10) Patent No.: US 7,315,611 B2
(45) Date of Patent: Jan. 1, 2008

(54) X-RAY REFLECTOR EXHIBITING TAPER, METHOD OF MAKING SAME, NARROW BAND X-RAY FILTERS INCLUDING SAME, DEVICES INCLUDING SUCH FILTERS, MULTISPECTRAL X-RAY PRODUCTION VIA UNISPECTRAL FILTER, AND MULTISPECTRAL X-RAY PRODUCTION VIA MULTISPECTRAL FILTER

(75) Inventors: Yong Min Cho, Silver Spring, MD (US); Thomas Joseph Fox, Virginia Beach, VA (US)

(73) Assignee: Monochromatic X-Ray Technologies, Inc., Lanham, MD (US)

(*) Notice: Subject to any disclaimer, the term of this patent is extended or adjusted under 35 U.S.C. 154(b) by 0 days.

(21) Appl. No.: 11/139,655

(22) Filed: May 31, 2005

(65) Prior Publication Data

US 2006/0002512 A1 Jan. 5, 2006

(51) Int. Cl.
*G21K 3/00* (2006.01)

(52) U.S. Cl. .................. 378/158; 378/159; 378/157; 378/156

(58) Field of Classification Search ............ 378/70, 378/82–90, 156–159, 210, 43, 16; 359/359, 359/360, 584–590, 592–598
See application file for complete search history.

(56) References Cited

U.S. PATENT DOCUMENTS

| 4,519,503 | A | | 5/1985 | Wilson |
| 4,969,175 | A | * | 11/1990 | Nelson et al. ............... 378/146 |
| 5,016,267 | A | | 5/1991 | Wilkins |
| 6,278,764 | B1 | * | 8/2001 | Barbee et al. ................ 378/84 |
| 2001/0028699 | A1 | * | 10/2001 | Iwasaki ........................ 378/84 |
| 2003/0128810 | A1 | | 7/2003 | Verman et al. |

OTHER PUBLICATIONS

International Search Report for PCT/US04/17131 dated Jan. 17, 2006.
Written Opinion of the International Searching Authority for PCT/US04/17131 dated Jan. 17, 2006.
"Thin film multilayer fan-beam X-ray monochromator," R.J. Harms, P.J. Serlemitsos, and S.M. Owens, *Proceedings of SPIE*, vol. 4501, No. 27, 2001, pp. 193-200.

(Continued)

Primary Examiner—Edward J. Glick
Assistant Examiner—Anastasia S. Midkiff
(74) Attorney, Agent, or Firm—Harness, Dickey & Pierce, P.L.C.

(57) ABSTRACT

An x-ray reflector may include: a substrate; a first layer formed on the substrate, the first layer including a relatively higher-Z material, where Z represents the atomic number; and a second layer formed on the first layer, the second layer including a relatively lower-Z material; at least one of the first layer and the second layer exhibiting a taper in an axial direction extending between a first end of the substrate and a second end of the substrate.

29 Claims, 15 Drawing Sheets

(see section line VIIA-VIIA' of Fig. 7B)

OTHER PUBLICATIONS

"X-ray monochromator for divergent beam radiography using conventional and laser produced X-ray sources," H.W. Schnopper, S. Romaine, and A. Krol, *Proceedings of SPIE*, vol. 4502, No. 24, 2001, pp. 19-29.

"Masked deposition techniques for achieving multilayer period variations required for short-wavelength (68Å) soft-x-ray imaging optics," J.B. Kortright, E.M. Gullikson, and P.E. Denham, *Applied Optics*, Optical Society of America, vol. 32, No. 34, Dec. 1, 1993, pp. 6961-6968.

"Development of Thermally Formed Glass Optics for Astronomical Hard X-ray Telescopes," W. Craig et al., *Optics Express*, vol. 7, No. 4, Aug. 14, 2000, pp. 178-185.

"Development and production of hard X-ray multilayer optics for HEFT," J.E. Koglin et al., *Proceedings of SPIE*, vol. 4851, 2003, pp. 607-618.

"Development of precision hard X-ray multilayer optics with sub-arcminute performance," J.E. Koglin et al, *Proceedings of SPIE*, vol. 4851, 2003, pp. 673-683.

"Fabrication and Performance of Constellation-X Hard X-ray Telescope Prototype Optics Using Segmented Glass," C.J. Hailey et al., *Proceedings of SPIE*, vol. 5168, 2004, pp. 90-99.

"X-ray and far UV multilayer mirrors: principles and possibilities," A.V. Vinogradov and B. Ya. Zeldovich, *Applied Optics*, vol. 16, No. 1, Jan. 1977, pp. 89-93.

Spiller, Eberhard, *Soft X-ray Optics*, SPIE Optical Engineering Press, Bellingham, 1994, pp. 139-168, also v-viii and 275-278.

PCT International Search Report (PCT Article 18 and Rules 43 and 44) dated Feb. 1, 2007, for corresponding PCT Application No. PCT/US06/19602.

* cited by examiner (see section line VIIA-VIIA' of Fig. 7B)

(top view)

X-RAY REFLECTOR EXHIBITING TAPER, METHOD OF MAKING SAME, NARROW BAND X-RAY FILTERS INCLUDING SAME, DEVICES INCLUDING SUCH FILTERS, MULTISPECTRAL X-RAY PRODUCTION VIA UNISPECTRAL FILTER, AND MULTISPECTRAL X-RAY PRODUCTION VIA MULTISPECTRAL FILTER

PRIORITY INFORMATION

This application claims priority according to 35 U.S.C. §120 upon a non-provisional U.S. patent application having Ser. No. 10/857,927 (hereafter, the "copending '927 application"), filed Jun. 2, 2004,which claims priority according to 35 U.S.C. §119(e) upon a provisional U.S. Patent Application having Ser. No. 60/651,460, filed Jun. 3, 2003, and also upon a non-provisional U.S. patent application having Ser. No. 11/132,305 and ((hereafter, the "copending '305 application"), filed May 19, 2005, which claims priority upon the copending '927 application, the disclosures of the above-identified patent applications being incorporated herein in their respective entireties.

BACKGROUND OF THE PRESENT INVENTION

X-rays are a form of electromagnetic radiation with wavelengths in the region of about 0.01 to 10 Angstroms (Å). These wavelengths are short compared to that of visible light, which has wavelengths in the range of about 4000 Å to 7000 Å. Visible light can be easily controlled and focused using known reflective and refractive optics. Visible light optic components do not work with x-rays because x-ray wavelengths approach the dimensions of distances between atoms in solids.

It is known that x-rays are diffraction scattered in all directions by single atoms. If the atoms are arranged substantially in multiple parallel planes (such as the planes in a crystal), there is an opportunity for the scattered x-rays from different planes to interfere constructively with one another. Scattered rays which obey Bragg's Law (described below) will appear to be reflected from the planes. This phenomenon is widely used in the study of crystal structures by x-ray diffraction.

It is also possible to diffract (reflect) x-rays using thin films of alternating layers of high-Z material and low-Z material, where Z is the atomic number of the metal and where the spacing between the layers is on the order of Angstroms. The nanolayers which form such films are analogous to the planes in a perfect single crystal, and scatter x-rays according to the same laws of physics. The effect of diffraction (reflection) from a such a multilayer coating is shown below in FIG. 1.

In FIG. 1. an incident beam 102 of x-rays impinges at an incident angle 112 of magnitude Θ upon a multilayer coating that includes layers 104, 106, 108 and 110 which are uniformly spaced a distance d apart from each other, respectively. Some of the x-rays of beam 102, representing a beam 116 of lesser intensity than beam 102, are diffracted (reflected) at a scattering angle 114 of the same magnitude, Θ. Some of x-rays of beam 102 pass through layer 104 as beam 102' to layer 106. Upon reaching layer 106, some the x-rays of beam 102' are diffracted (reflected) as a lower intensity beam 116' again at the same scattering angle Θ, while some pass through layer 106 as beam 102" to layer 108. Upon reaching layer 108, some the x-rays of beam 102" are diffracted (reflected) as a lower intensity beam 116" at the scattering angle Θ, while some pass through layer 108 as beam 102''' to layer 110. Similarly, at least some of the x-rays of beam 102''' are diffracted (reflected) by layer 110 at the scattering angle Θ as a lower intensity beam 116''', while some (not depicted) may pass through layer 110 and subsequent layers (if present).

Bragg's law describes the condition of diffraction (reflection) depicted in FIG. 2. Bragg's law is as follows.

$$n\lambda = 2d \sin\Theta \tag{1}$$

Here, again, $\lambda$ is the x-ray wavelength, d is the spacing between the layers, Θ is the incident angle (also described as the grazing angle) and n is any non-zero positive integer representing the number of pairs of respective layers of high-Z and low-Z material . By carefully choosing the spacing, d, and the incident angle, Θ, the wavelength, $\lambda$, of the diffracted (reflected) light can be controlled to produce specific narrow bandwidths of x-rays.

Bragg's law is applied in the copending '927 application, where a sheaf 246 of stacked rectangular reflectors can act as a filter to produce a narrow band of x-rays, as is depicted in Background Art FIG. 2 according to the copending '927 application. There, a broad band beam 257 of x-rays is depicted as originating from a source 256 and impinging upon a front end of simplified sheaf 246 of reflectors. While sheaf 246 includes a total of 1, 2, . . . , N reflectors, its depiction is simplified, e.g., in the sense that only reflectors 232-N, 232-N-1 and 232-N-2 are depicted. Another simplification, e.g., is that no structures that establish relative spacing between adjacent reflectors 232-i and 232-i-1 are depicted. Further simplifications in FIG. 2 are that relative proportions, e.g., between distances lfi, lli, df1 & dri and $i^{th}$ thicknesses of the reflectors, respectively, and angles α1i and α2i, respectively, are not to scale.

In FIG. 2, an $i^{th}$ distance, di, between front ends of any two adjacent reflectors is substantially the same, i.e., the distance df1 between front ends of reflectors 232-N & 232-N-1 substantially equals the distance df2 between front ends of reflectors 232-N-1 & 232-N-2, etc., namely df1≈df2 . . . . To ensure that each reflector is oriented so that the front end thereof experiences substantially the same incident angle of x-rays, adjacent reflectors are rotated relative to one another. More particularly, to ensure that α1'≈α1, reflector 232-N-1 is rotated a non-zero angle β2 relative to, e.g., horizontal, where it is assumed in FIG. 2 that reflector 232-N is oriented to be horizontal, i.e., its angle, β1, is zero (β1=0). Similarly, so that α1"=α1', reflector 232-N-2 is rotated an angle β3, where β3>β2, etc. Thus, in FIG. 2, the following is true.

$$\alpha 1 \approx \alpha 1' \approx \alpha 1'' \tag{2}$$

Despite such relative rotation, however, distance, dri, between the rear ends of adjacent reflectors 232-i & 232-i-1 is substantially the same, i.e., a distance dr1 between reflectors 232-N & 232-N-1 is substantially the same as a distance dr2 between adjacent reflectors 232-N-1 & 232-N-2, etc., namely dr1 dr2 . . . .

As a consequence of such relative rotation, the distance dfi between front ends of adjacent reflectors 232-i & 232-i-1 is significantly smaller than the distance dri between rear ends of adjacent reflectors 232-i & 232-i-1, which can be restated as follows.

$$dfi < dri \tag{3}$$

Returning to Bragg's law, it describes the wavelength, λi, diffracted (reflected) at an $i^{th}$ point along a reflecting side 233-i of each reflector 232-i. Thus, a wavelength diffracted (reflected) at the front end of reflector 232-i, namely wavelength $\lambda_f$, would be as follows.

$$\lambda_f = \frac{2t_{fi}\sin\alpha 1i}{n} \quad (4)$$

where $t_{fi}$ is a thickness of the reflecting layers at the front end of reflector 232-i, $\alpha 1i$ is the incidence angle at the front end of reflector 232-i, and n is the number of reflecting layer interfaces in reflector 232-i. Similarly, a wavelength diffracted (reflected) at the rear end of reflector 232-i, namely wavelength $\lambda_r$, would be as follows.

$$\lambda_r = \frac{2t_{ri}\sin\alpha 2i}{n} \quad (5)$$

where $t_{ri}$ is a thickness of the reflecting layers at the rear end of reflector 232-i, $\alpha 2i$ is the incidence angle at the rear end of reflector 232-i, and n (again) is the number of reflecting layer interfaces in reflector 232-i.

SUMMARY OF THE PRESENT INVENTION

An embodiment of the present invention provides an x-ray reflector. Such an x-ray reflector may include: a substrate; a first layer formed on the substrate, the first layer including a relatively higher-Z material, where Z represents the atomic number; and a second layer formed on the first layer, the second layer including a relatively lower-Z material; at least one of the first layer and the second layer exhibiting a taper in an axial direction extending between a first end of the substrate and a second end of the substrate.

An embodiment of the present invention provides a method of making such an x-ray reflector.

An embodiment of the present invention provides such a filter to produce a unispectral narrow band beam of x-rays.

An embodiment of the present invention provides a multispectral version of such a filter to produce at least two narrow band beams of x-rays.

An embodiment of the present invention provides a method of making a such an x-filter.

An embodiment of the present invention provides an apparatus to produce one or more narrow band beams of x-rays, e.g., using such an x-ray filter.

An embodiment of the present invention provides a radiographic x-ray imaging device that includes, e.g., such an apparatus that can produce the one or more narrow band beams of x-rays.

An embodiment of the present invention can achieve multispectral x-ray production via a unispectral filter.

DETAILED DESCRIPTION OF EXAMPLE EMBODIMENTS

Figure 1:
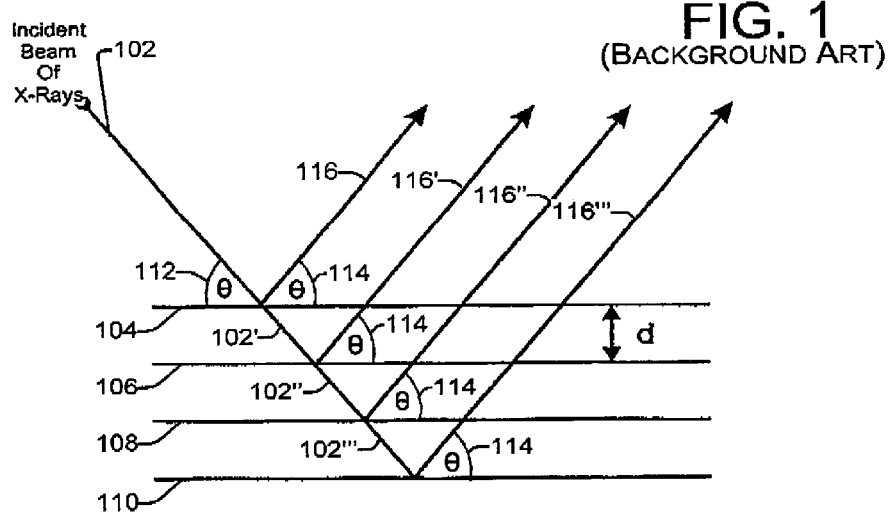
FIG. 1 is a diagram of x-ray diffraction (reflection) by a multi-layer coating according to the Background Art.

The present invention will be described more fully with reference to the accompanying drawings, in which example embodiments of the present invention are shown. It should be understood, however, that example embodiments of the present invention described herein can be modified in form and detail without departing from the spirit and scope of the present invention. Accordingly, the embodiments described herein are provided by way of example and not of limitation, and the scope of the present invention is not restricted to the particular embodiments described herein.

In particular, the relative thicknesses and positioning of structures or regions may be reduced or exaggerated for clarity. In other words, the figures are not drawn to scale. Further, a structure is considered as being formed "on" another structure when formed either directly on the referenced structure or formed on other structures overlaying the referenced structure.

Reference number similarities from one figure to the next suggest at least similar components/items.

In developing embodiments of the present invention, the following observation regarding the Background Art sheaf of reflection units was made, and a path to an alternate construction of a sheaf of reflection units identified. While sheaf 246 of Background Art FIG. 2 (according to the copending '927 application) can filter broad band beam 257 to produce a narrow band of x-rays, the relative rotation of reflector units 232-i (again, done to maintain $\alpha 1 \approx \alpha 1' \approx \alpha 1''$. . . , see Equation No. (4) above) results in dfi<dri (see Equation No. (5) above), which means that the wavelength $\lambda_f$ diffracted (reflected) at the front end of reflector 232-i will differ somewhat from the wavelength $\lambda_r$ diffracted (reflected) at the rear end of reflector 232-i. There are instances in which it can be desirable to reduce (if not substantially eliminate) the degree to which $\lambda_f$ and $\lambda_r$ differ. One or more embodiments of the present invention provides a sheaf of reflectors that can reduce (if not substantially eliminate) the degree to which $\lambda_f$ and $\lambda_r$ differ.

To reduce (if not substantially eliminate) the degree to which $\lambda_f$ and $\lambda_r$ differ, i.e., to obtain $\lambda_f \approx \lambda_r$, we return to Bragg's law, combining Equation Nos. (4) above and (5) above to yield the following.

$$\lambda_r \approx \lambda_f \quad (6)$$
$$\left( = \frac{2t_{ri}\sin\alpha 2i}{n} \right) \approx \left( = \frac{2t_{fi}\sin\alpha 1i}{n} \right)$$

Equation No. (6) can be rearranged as follows.

$$\frac{t_{fi}}{t_{ri}} \approx \frac{\sin\alpha 1i}{\sin\alpha 2i} \quad (7)$$

Here, $\alpha 1i$ and $\alpha 2i$ are substantially fixed values, so that leaves manipulation of $t_{fi}$ (again, the thickness of the reflecting layers at the front end of reflector 232-i) and $t_{ri}$ (again, the thickness of the reflecting layers at the rear end of reflector 232-i) as a basis for obtaining $\lambda_f \approx \lambda_r$.

It should understood that Equation No. (7) above will change the shape of the reflecting layers in reflector 232-i from being rectangular to trapezoidal. This is depicted in FIG. 3A, and in more detail in FIG. 3B.

Figure 3A:
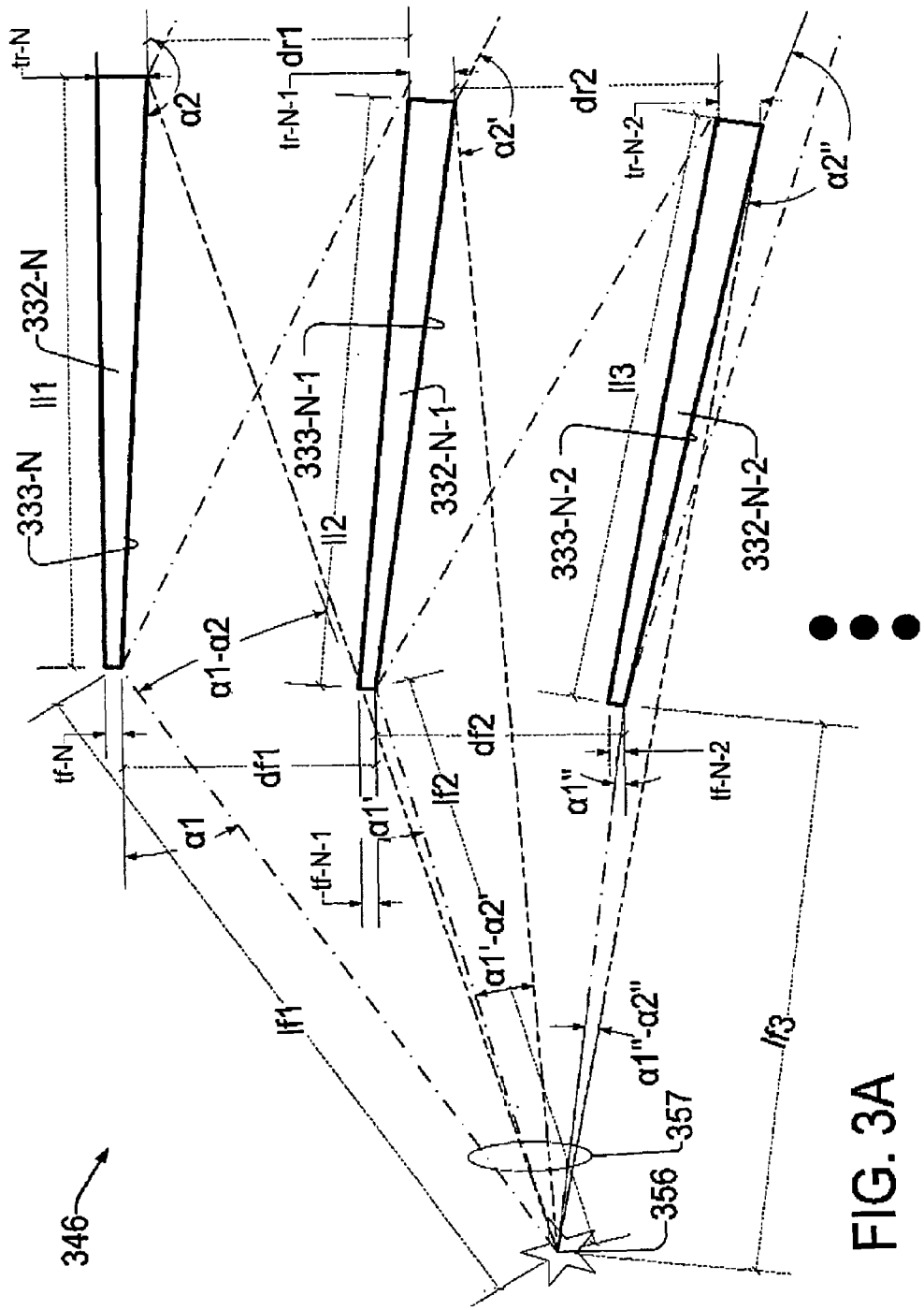
FIG. 3A is a diagram of a sheaf of x-ray reflectors relative to an x-ray source, according an embodiment of the present invention

FIG. 3A is a diagram of a sheaf 346 of x-ray reflectors relative to an x-ray source, according an embodiment of the present invention In FIG. 3A, a broad band beam 357 of x-rays is depicted as originating from a source 356 and impinging upon a front end of simplified sheaf 346 of reflectors. While sheaf 346 includes a total of N reflectors, its depiction is simplified, e.g., in the sense that only reflectors 332-N, 332-N-1 and 332-N-2 are depicted. Another simplification, e.g., is that no structures that establish relative spacing between adjacent reflectors 332-i and 332-i-1 are depicted. Such spacing structures (or bodies) can be found in the copending '305 application and in the copending '927 application. Further simplifications in FIG. 3 are that relative proportions, e.g., between distances lfi, lli, df1 & dri and $i^{th}$ thicknesses of the reflectors, respectively, and angles $\alpha 1i$ and $\alpha 2i$, respectively, are not to scale.

Figure 2:
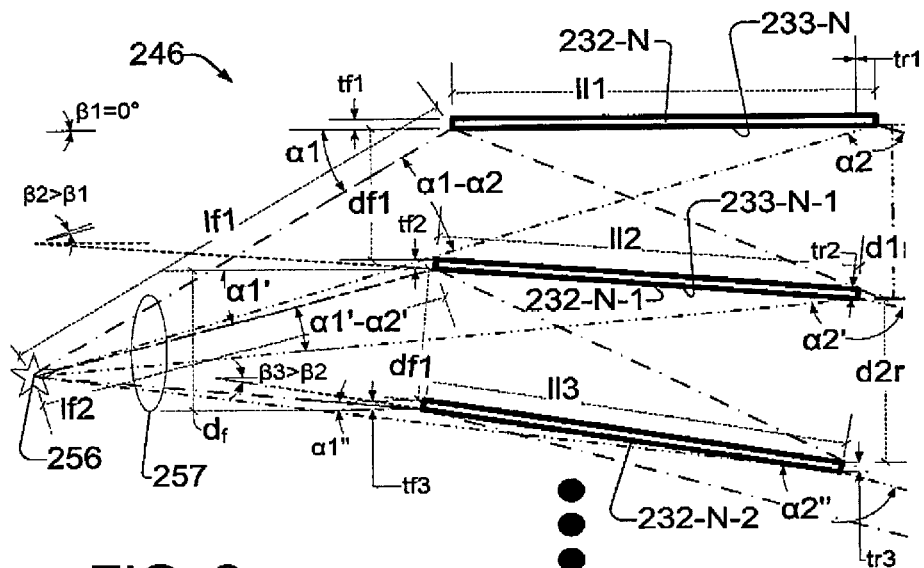
FIG. 2 is a diagram of a sheaf of x-ray reflectors relative to an x-ray source, according to the Background Art.

FIG. 3A is similar in many respects to Background Art FIG. 2 (again, according to the copending '927 application). Some of the similarities will be briefly reviewed. A sheaf 346 of stacked reflectors (albeit having a trapezoidal, not rectangular, silhouette) is depicted in FIG. 3A, where sheaf 346 can act as a filter to produce a narrow band of x-rays from a broad band beam 357 of x-rays. In FIG. 3A, an $i^{th}$ distance, di, between front ends of any two adjacent reflectors is substantially the same, i.e., the distance df1 between front ends of reflectors 332-N & 332-N-1 substantially equals the distance df2 between front ends of reflectors 332-N-1 & 332-N-2, etc., namely df1≈df2, etc. To ensure that each reflector is oriented so that the front end thereof has substantially the same incident angle of x-rays, adjacent reflectors are rotated relative to one another. More particularly, to ensure that $\alpha 1' \approx \alpha 1$, reflector 332-N-1 is rotated a non-zero angle $\beta 2$ (not shown in FIG. 3A) relative to, e.g., horizontal, where it is assumed in FIG. 3 that reflector 332-N is oriented to be horizontal, i.e., its angle, $\beta 1$ (not shown in FIG. 3A), is zero ($\beta 1=0$). Similarly, so that $\alpha 1''=\alpha 1'$, reflector 332-N-2 is rotated an angle $\beta 3$ (not shown in FIG. 3A), where $\beta 3>\beta 2$, etc. Thus, in FIG. 3, the following is true.

$$\alpha 1 \approx \alpha 1' \approx \alpha 1'' \quad (8)$$

Despite such relative rotation, however, distance, dri, between the rear ends of adjacent reflectors 332-i & 332-i-1 is substantially the same, i.e., a distance dr1 between reflectors 332-N & 332-N-1 is substantially the same as a distance dr2 between adjacent reflectors 332-N-1 & 332-N-2, etc., namely dr1≈dr2 . . . .

As a consequence of such relative rotation and despite the trapezoidal shape of each reflector 332-i (to be discussed in more detail below), the distance dfi between front ends of adjacent reflectors 332-i & 332-i-1 is significantly smaller than the distance dri between rear ends of adjacent reflectors 332-i & 332-i-1, which can be restated as follows.

$$dfi<dri \quad (9)$$

Figure 3B:
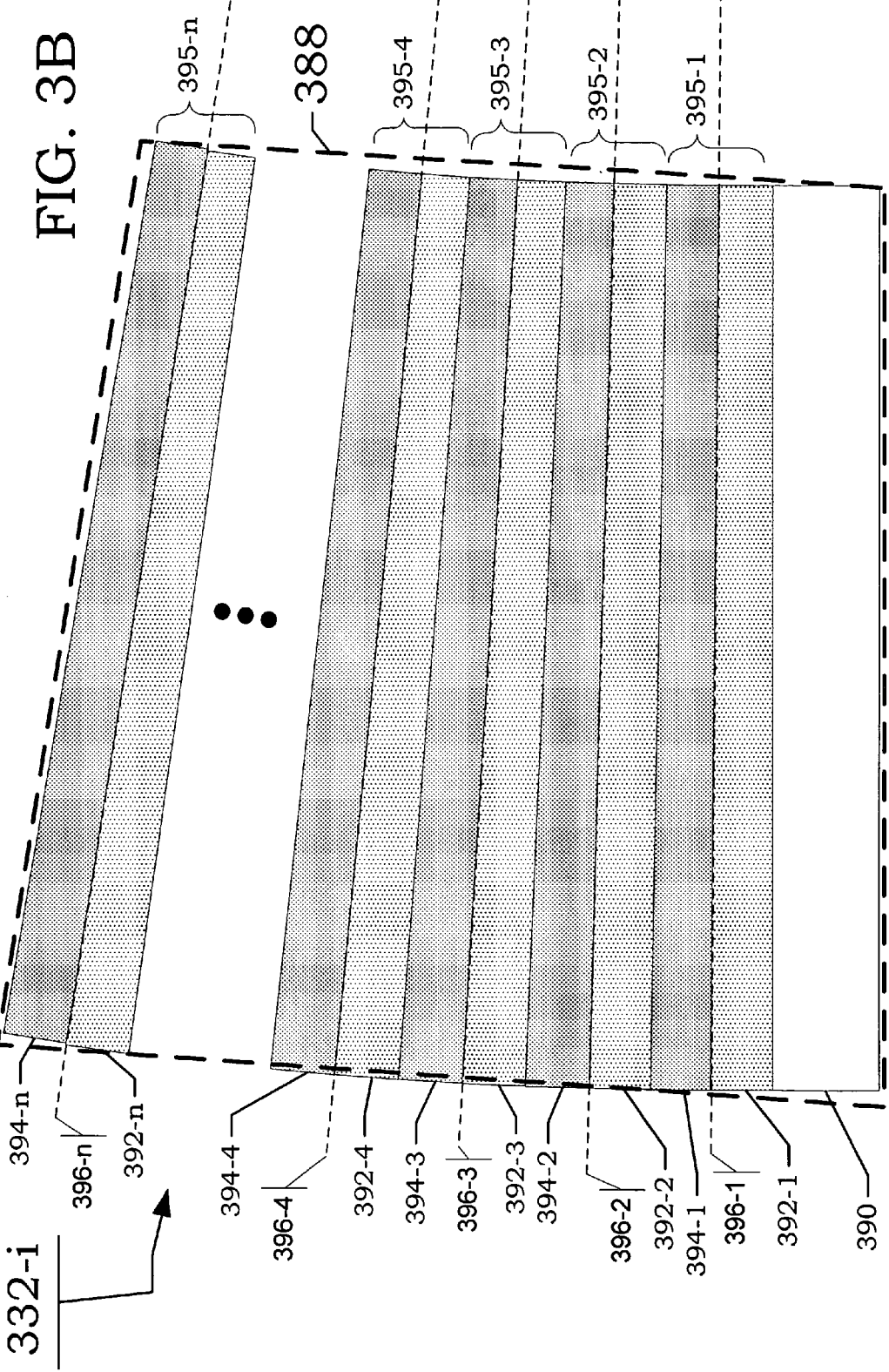
FIG. 3B is an exploded view of an $i^{th}$ reflector in FIG. 3A albeit rotated about 180°, according to an embodiment of the present invention.

FIG. 3B is an exploded view of an $i^{th}$ reflector 332-i in FIG. 3A albeit rotated about 180°, according to an embodiment of the present invention.

In FIG. 3B, reflector 332-i includes: a structural substrate 390; a first layer 392-1 formed of a high-Z material (where, again, Z is the atomic number of the metal) and formed on structural substrate 390; and a first layer 394-1 formed of a low-Z material and formed on first layer 392-i. Together, layers 392-i and 394-i can be described as representing a bi-layer structure 395-i. An interface 396-1 between the first high-Z layer 392-1 and the first low-Z layer 394-1 defines a reflecting surface. Multiple pairs of a high-Z layer 392-i and a low-Z layer 394-i, i.e., multiple bi-layer structures 395-i, can be stacked one on the other in a typical reflector 332-i. For example, the number of stacked bi-layer structures 395-i can be in a range of 1-300, or more particularly, e.g., 2-200, etc. In FIG. 3B, a second bi-layer structure 395-2, formed of second high-Z layer 392-2 and second low-Z layer 394-2 with an interface 396-2 therebetween, is stacked on first bi-layer structure 395-1. A third bi-layer structure 395-3, formed of third high-Z layer 392-3 and third low-Z layer 394-3 with an interface 396-3 therebetween, is stacked on second bi-layer structure 395-2. This continues until a last bi-layer structure 395-n, formed of an $n^{th}$ high-Z layer 392-n and an $n^{th}$ low-Z layer 394-n with an $n^{th}$ interface 396-n therebetween, is stacked on the next to last bi-layer structure (not depicted in FIG. 3B).

Structural substrate 390 can be, e.g., a metal such as aluminum (AL) or glass (the latter exhibiting a smoother surface). Each $i^{th}$ layer 392-i can be, e.g., a metal such as gold (Au), platinum (Pt) and/or iridium (Ir), etc. Each $i^{th}$ layer 394-i can be, e.g., carbon (C), e.g., pure carbon.

Each high-Z layer 392-i and each corresponding low-Z layer 394-i can have substantially the same trapezoidal silhouette, which causes reflector 332-i overall to take on a trapezoidal silhouette 388. Though FIG. 3B is drawn as if a thickness of each such trapezoidal shape tapers linearly, it is to be recalled that the taper progresses from the rear end to the front end of each trapezoidal shape according to Equation No. (7) above, which is a non-linear expression. However, as a practical matter in typical circumstances, the angles α1i and α2i each are small (e.g., both can be less than or equal to about 0.5°), which results in an $i^{th}$ front end thickness tfi and a corresponding $i^{th}$ rear end thickness tri that (while significantly different) are not substantially different. Alternatively, especially in view of the small dimensions, a linear taper could be used as an approximation of the non-linear taper.

To restate, each high-Z layer 392-i and each corresponding low-Z layer 394-i can have substantially the same taper. But high-Z layer 392-i does not necessary have the same thickness at a given axial location as corresponding low-Z layer 394-i. For example, relative to a reference axis corresponding to an intersection of interface 396-i and the plane of the page on which FIG. 3A would be printed, at any given point along the reference axis, a thickness of high-Z layer 392-i can represent about ⅖ of the thickness of bi-layer structure 395-i, while a thickness of low-Z layer 394-i can represent about ⅗ of the thickness of bi-layer structure 395-i.

An example of one sample instantiation of a narrow band x-ray filter that includes a sheaf 346 of reflectors 332-i will be provided, but it is to be kept in mind that the explicit dimensions are not limiting of the present invention as other combinations of dimensions are contemplated. Thus, a sample filter can have the following specific dimensions in order to produce substantially monochromatic, e.g., 18 keV x-rays (or, in other words, $\lambda \approx 0.69 Å$). A focal length of the filter, i.e., a distance lfi to a front edge of each reflector 332-i from source 356 can be about 6 inches. Incidence angle α1i at the front end of reflector 332-i can be about 0.5°. Incidence angle at the rear end of reflector 332-i can be about 0.3°. The length lli of substrate 390 can be about four inches, with a thickness of about 0.004 inches (keeping in mind that substrate 390 can be substantially rectangular). A distance dfi between front ends of adjacent reflectors 332-i and 332-i-1 can be about 0.021 inches. A distance dri between rear ends of adjacent reflectors 332-i and 332-i-1 can be about 0.035 inches. The number, n, of pairs of high-Z layer 392-i and corresponding low-Z layer 394-i can be twelve, i.e., n=12. A thickness of the n=12 pairs of pairs of high-Z layer 392-i and corresponding low-Z layer 394-i at the front end of reflector 332-i can be about 30Å. A thickness of the n=12 pairs of pairs of high-Z layer 392-i and corresponding low-Z layer 394-i at the rear end of reflector 332-i can be about 70Å. At any given axial location, the thickness of high-Z layer 392-i can be about ⅖ of the thickness of the bi-layer structure 395-i. At any given axial location, the thickness of low-Z layer 394-i can be about ⅗ of the thickness of the bi-layer structure 395-i. High-Z layer 392-i can be formed of platinum (Pt), while low-Z layer 394-i can be formed of pure carbon.

Figure 4A:
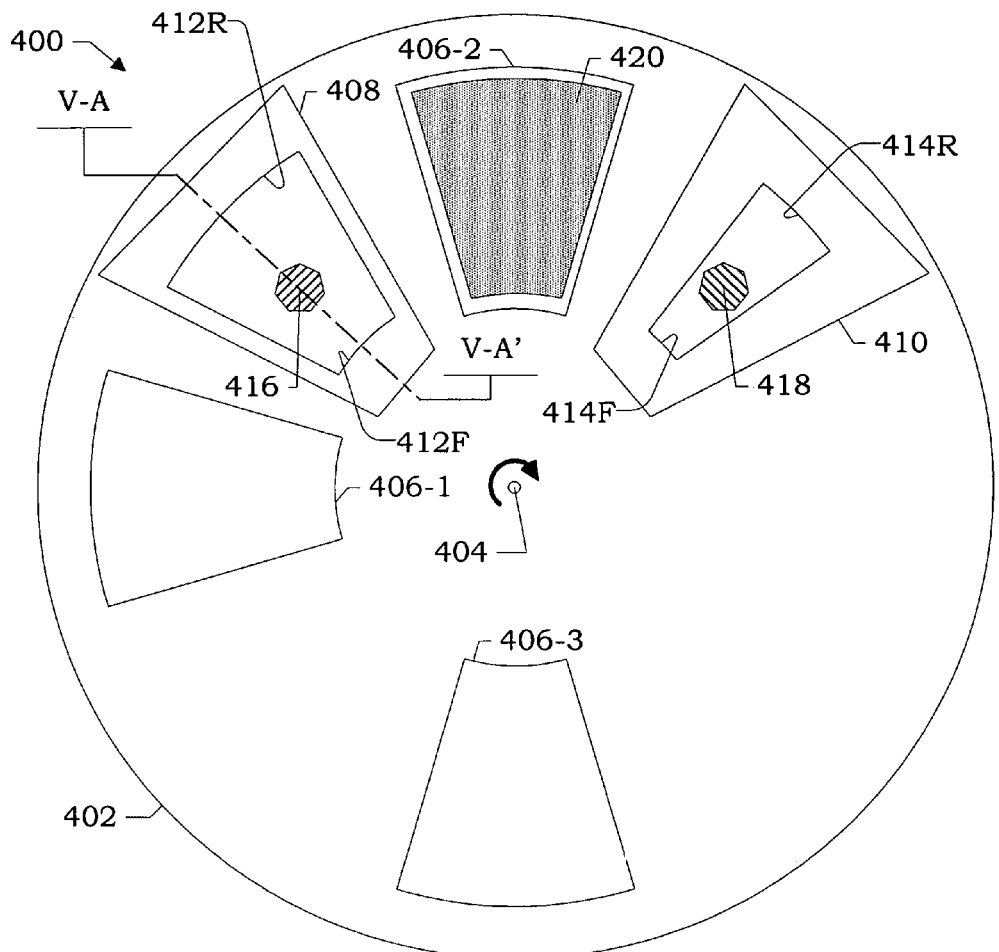
FIG. 4A is a top view of an arrangement used to produce tapered coating reflectors, according to an embodiment of the present invention.
Figure 5A:
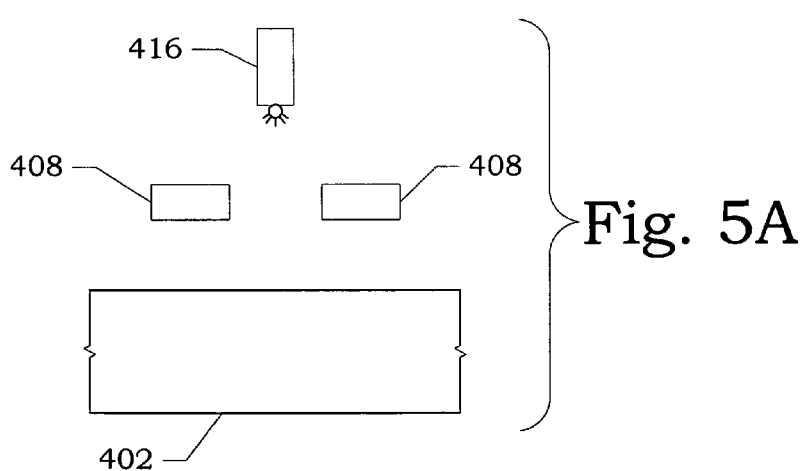
FIG. 5A is a sectional view of the arrangement of FIG. 4A, taken along view line VA-VA' shown in FIG. 4A.

FIG. 4A is a top view of an arrangement 400 used to produce tapered coating reflectors, such as reflector 332-i, according to an embodiment of the present invention. FIG. 5A is a sectional view of the arrangement of FIG. 4A, taken along view line VA-VA' shown in FIG. 4A.

In FIG. 4A, arrangement 400 includes a round platform 402 that has an axis of rotation 404 (with, e.g., clockwise rotation being assumed) and three structural substrates 406-1, 406-2 and 406-3, each corresponding to structural substrate 390. The silhouette of each structural substrate 406-i is generally fan-shaped or trapezoidally-shaped. The front (or, in terms of the orientation of FIG. 4A, radially inward) end as well as the rear (or, in terms of the orientation of FIG. 4A, radially outward) end of each structural substrate 406-i can be substantially circular arc-segments, respectively, where the front end's arc represents a smaller arc-segment than the rear end's arc. As such, each structural substrate 406-i can be described as an annular segment. As an alternative, the front end and/or the rear end can be configured as substantially planar surfaces, or some other shape.

For simplicity of illustration, only three structural substrates 406i have been depicted in FIG. 4A. Also for simplicity of illustration, structural substrates 406-1, 406-2 and 406-3 have been depicted as if arrayed at about the 9:00, 12:00 and 6:00 o'clock locations, respectively. Other numbers of structural substrates are contemplated, as are other locations of such structural substrates on rotating platform 402.

Arrangement 400 of FIG. 4A further includes a high-Z material source 416, e.g., a sputterer, and a low-Z material source 418, e.g., a sputterer. Sources 416 and 418 are disposed over platform 402, as can be seen in FIG. 5A. While platform 402 is rotatable, sources 416 and 418 can be substantially fixed in location, at least rotationally when contrasted with platform 402.

Arrangement 400 further includes a mask 408 and a mask 410 interposed between sources 416 and 418, respectively, and the underlying structure, as can be seen in FIG. 5A. Sources 416 and 418 are aligned with respect to masks 408 and 410 so that masks 408 and 410 can control the pattern of material projected by sources 416 and 418. While platform 402 is rotatable, masks 408 and 410 are substantially fixed in location, at least rotationally when contrasted with platform 402. Moreover, masks 408 and 410 are aligned underneath sources 416 and 418, respectively.

Similar to the silhouette of each structural substrate 406-i, each of mask 408 and 410 can have an aperture that can be described as generally fan-shaped or trapezoidally-shaped. The front (or, in terms of the orientation of FIG. 4A, radially inward) end surfaces 412F & 414F and the rear (or, in terms of the orientation of FIG. 4A, radially outward) end surfaces 412R & 414R that form partial boundaries of the apertures in masks 408 and 410 can be substantially circular arc-segments, respectively, where the front ends' arc represents smaller arc-segments than the rear ends' arcs. As such, the apertures in masks 408 & 410 can be described as annular segments. As an alternative, the front end surfaces and/or the rear end surfaces can be configured as substantially planar surfaces, or some other shape.

More generally, the aperture shape (e.g., apertures 408 and 410) are determined according to characteristics of the process by which high-Z material and low-Z material is alternately formed onto a substrate. For example, a variation of platform 402 might exhibit variable speed such that apertures could be rectangular and yet there could result tapered coatings, etc.

In FIG. 4A, it is assumed that a previous orientation of platform 402 had disposed structural substrates 406-1, 406-2 and 406-3 at about the 6:00, 9:00 and 3:00 o'clock locations, respectively. It is further assumed in FIG. 4A that platform 402 has been rotated about 90° clockwise from the previous orientation.

As it was swept through the 90° of rotation, structural substrate 406-2 passed along an arcuate path beneath mask 408. During that interval, high-Z material projected from source 416 (and that had passed through the aperture in mask 408) became disposed on structural substrate 406-2. This resulted in the formation of a first layer of high-Z material, where such a layer is indicated by reference number 420.

Figure 4B:
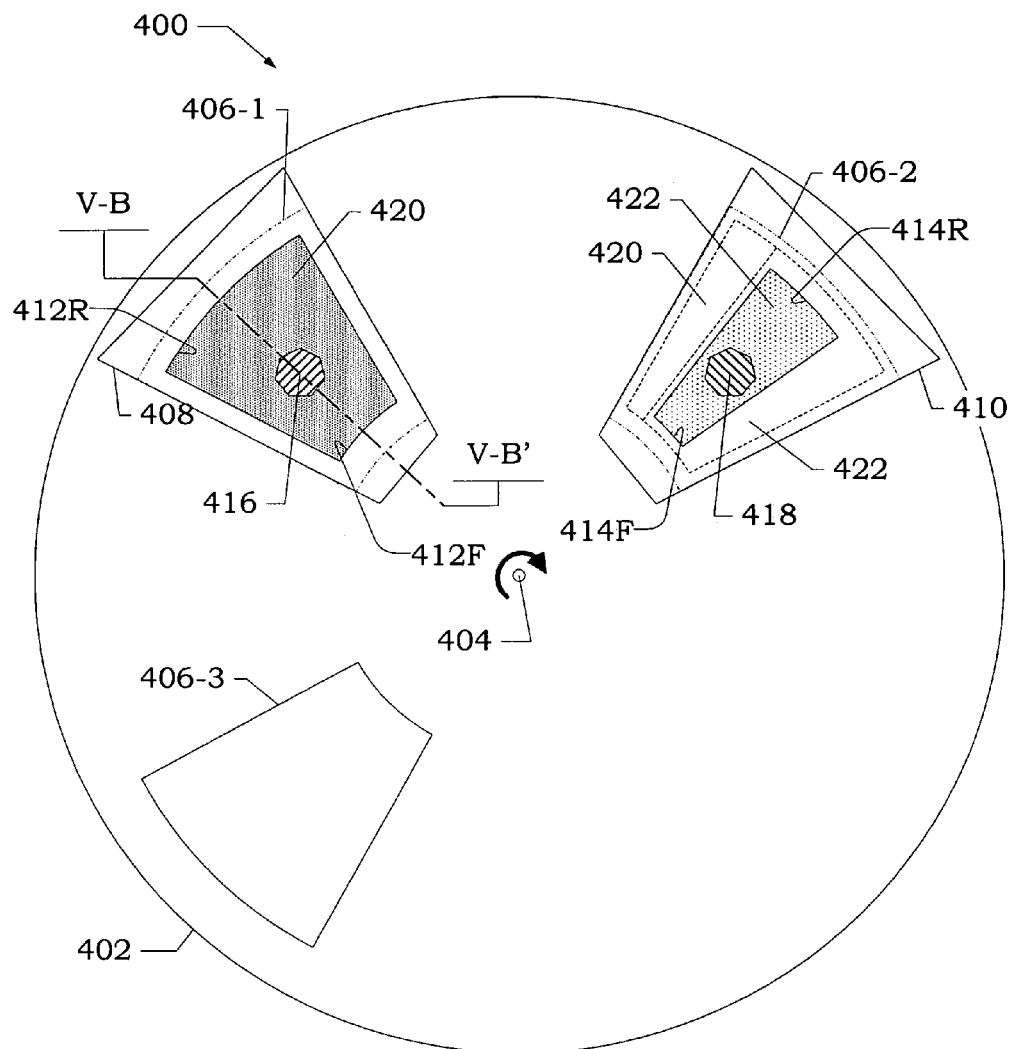
FIG. 4B is a top view of the arrangement of FIG. 4A, albeit with the platform having been rotated relative to FIG. 4A.
Figure 5B:
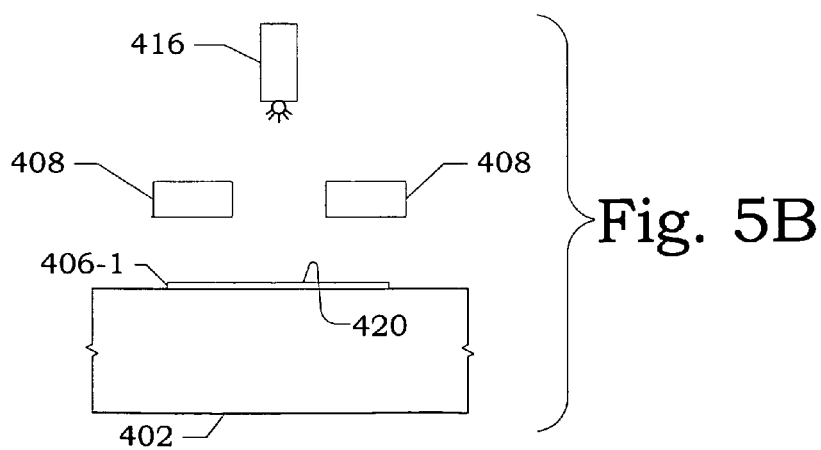
FIG. 5B is a sectional view of the arrangement of FIG. 4B, taken along view line VB-VB' shown in FIG. 4B.

FIG. 4B is a top view of arrangement 400, albeit with platform 402 having been rotated relative to FIG. 4A. FIG. 5B is a sectional view of arrangement 402, taken along view line VB-VB' shown in FIG. 4B.

More particularly, in FIG. 4B, platform 402 has been rotated about 45° clockwise relative to FIG. 4A. As such, structural substrates 406-1, 406-2 and 406-3 are disposed at about the 10:00-11:00, 1:00-2:00 and 7:00-8:00 o'clock locations, respectively. The result is that structural substrates 406-1 and 406-2 are disposed underneath masks 408 and 410, respectively. High-Z material projected from source 416 (and through the aperture in mask 408) has became disposed on structural substrate 406-1, resulting in the formation of a first layer of high-Z material, where such a layer is (again) indicated by reference number 420. Low-Z material projected from source 419 (and through the aperture in mask 410) has became disposed on the high-z material layer that previously was formed on structural substrate 406-1, resulting in the formation of a first layer of low-Z material, where such a layer is indicated by reference number 422. No layer is shown as having been formed on structural substrate 406-3 as it has not yet passed beneath on the sources 416 or 418.

Figure 4C:
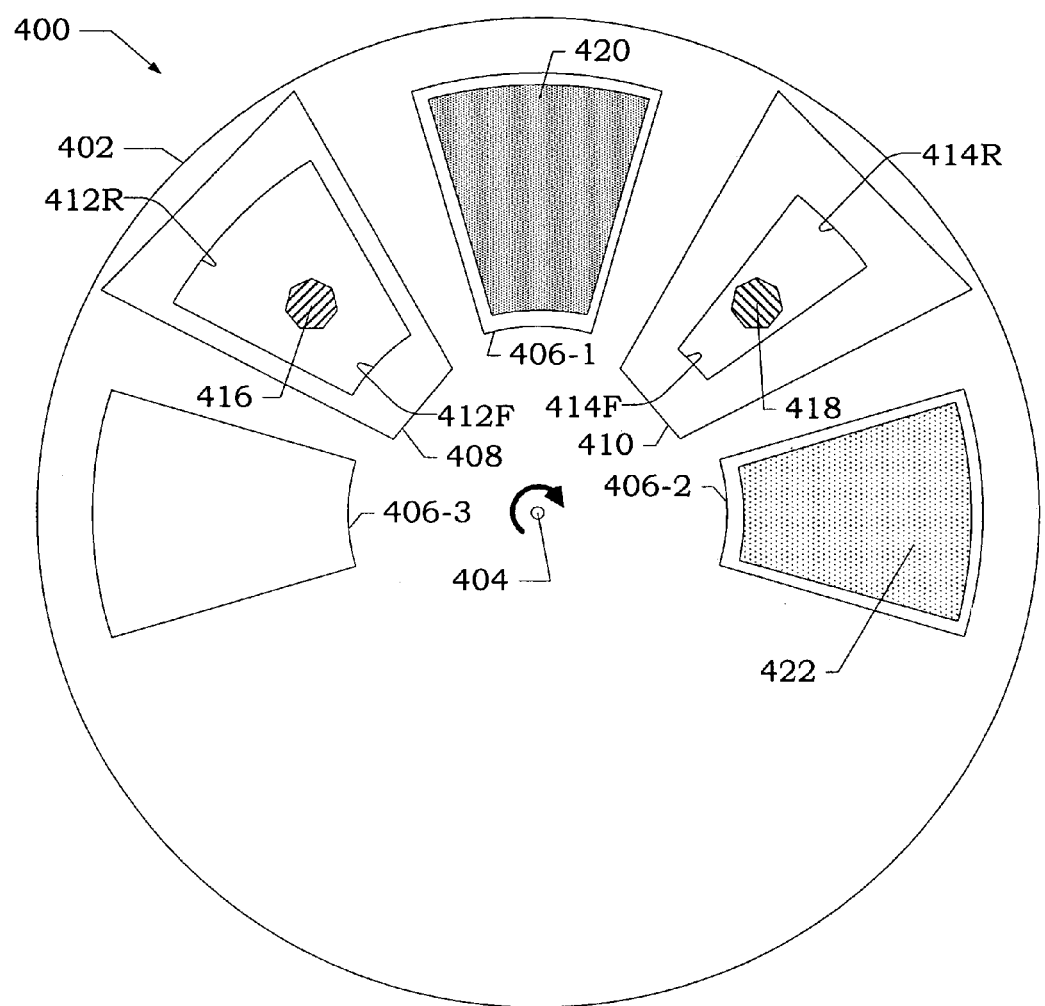
FIG. 4C is a top view of the arrangement of FIG. 4A, albeit with platform 402 having been rotated relative to FIG. 4B.

FIG. 4C is a top view of arrangement 400, albeit with platform 402 having been rotated relative to FIG. 4B.

More particularly, in FIG. 4C, platform 402 has been rotated about 45° clockwise relative to FIG. 4B. As such, structural substrates 406-1, 406-2 and 406-3 are disposed at about the 1200, 3:00 and 9:00 o'clock locations, respectively. The currently top-most layer formed on structural substrate 406-1 is a high-Z material layer 420. The currently top-most layer formed on structural substrate 406-2 is a low-Z material 422. Again, no layer is shown as having been formed on structural substrate 406-3 as it has not yet passed beneath on the sources 416 or 418.

The rotation depicted via FIGS. 4A-4C can be continued until each structural substrate 406-i has a sufficient number of alternating high-Z layers 420 and low-Z layers formed thereon so as to correspond to, e.g., reflector 332-i.

The tapering thickness of layers formed via the arrangement of FIGS. 4A-4C can be explained (without being bound by theory) as follows. Moving radially outward from axis of rotation 404, the width of apertures 408 and 410 also exhibit an inverse taper such that masks 408 and 410 are wider at the rear ends (located relatively more radially outward) than at the front ends (located relatively more radially inward), respectively. As a given underlying structural substrate 406-i moves arcuately past a given aperture 408/410, a length of time which a point thereon located a given radial distance (from axis of rotation 404) is exposed to material from source 416/418 depends upon the rate of rotation and the width of the aperture at the given radial distance. Assuming that the rate of rotation is substantially uniform and that the output from source 416/418 is substantially uniform, then the amount of deposition material that impinges upon the given structural substrate 606-i can be determined by the width of aperture 408/410 at the given radial distance. Because the width of apertures 408/410 is proportional to radial distance, the amount of material deposited on the given structural substrate 406-i is proportional to the radial distance, which results in a layer thickness that is proportional to radial distance. In other words, the arrangement results in an exposure time that tapers radially.

Arrangement 400 of FIGS. 4A-4C can be described as being based upon a horizontal disposition of each structural substrate 406-i. Other dispositions are contemplated. For example, FIG. 6 can be described as being similar to FIGS. 4A-4C albeit based upon a vertical disposition of the structural substrates. Further in the alternative (relative to FIG. 6), structural substrates can be inclined at an angle between vertical and horizontal such that resulting layer thicknesses are proportional to radius (in terms of spherical coordinates, where the origin can be located in the plane of the page relative to FIGS. 4A-4C at axis of rotation 404).

Figure 6:
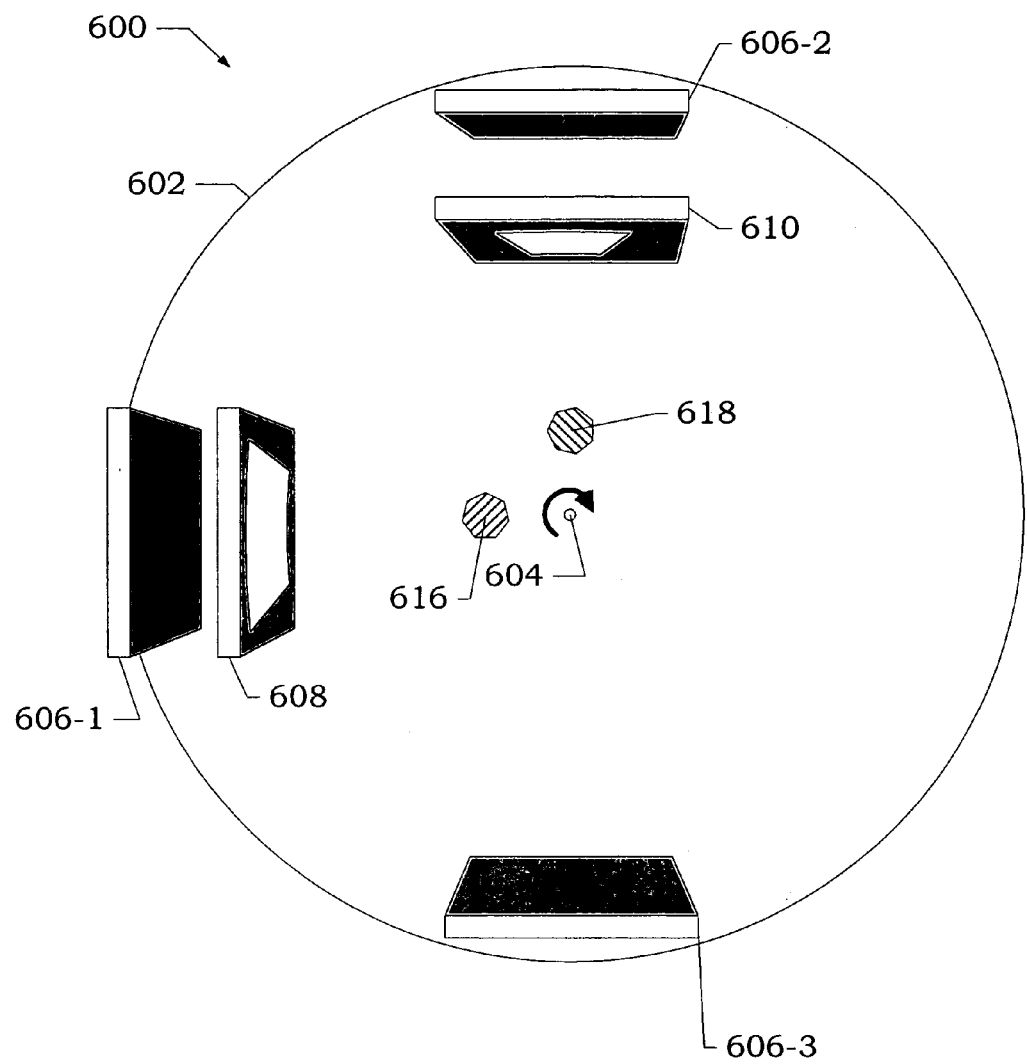
FIG. 6 is a top view of an arrangement used to produce tapered coating reflectors, according to an embodiment of the present invention.

FIG. 6 is a top view of an arrangement 600 used to produce tapered coating reflectors, such as reflector 332-i, according to an embodiment of the present invention.

In many respects, FIG. 6 is similar to FIGS. 4A-4C. Some of the similarities will be briefly reviewed. In FIG. 6A, arrangement 600 includes a round platform 602 that has an axis of rotation 604 (with, e.g., clockwise rotation being assumed); three structural substrates 606-1, 606-2 and 606-3, each corresponding to structural substrate 390, and masks 608 and 610. The silhouette of each structural substrate 606-i is generally fan-shaped or trapezoidally-shaped. For simplicity of illustration, only three structural substrates 606i have been depicted in FIG. 6A. Also for simplicity of illustration, structural substrates 606-1, 606-2 and 606-3 have been depicted as if arrayed at about the 9:00, 12:00 and 6:00 o'clock locations, respectively. Other numbers of structural substrates are contemplated, as are other locations of such structural substrates on rotating platform 602.

As alluded to above, structural substrates 606-1, 606-2 and 606-3 can be described as vertically disposed, or being oriented vertically, as contrasted with FIGS. 4A-4C. The front end (or, in terms of the orientation of FIG. 6A, the end proximal to platform 602) and the rear end (or, in terms of the orientation of FIG. 6A, the end distal to platform 602) of each structural substrate 606-i can be substantially circular arc-segments, respectively, where the front end arc represents a smaller arc-segment than the rear end arc. As such, each structural substrate 606-i can be described as an annular segment. As an alternative, the front end and/or the rear end can be configured as substantially planar surfaces, or some of other shape.

Mask 608 and mask 610 are, in effect, interposed at certain angles (during rotation) between sources 616 & 618, respectively, and respective structural substrates 606-i. Sources 616 and 618 are aligned with respect to masks 608 and 610 so that masks 608 and 610 can control the pattern of material projected by sources 616 and 618. While platform 602 is rotatable, masks 608 and 610 are substantially fixed in location, at least rotationally when contrasted with platform 602.

Each of masks 608 and 610 can have an aperture that can be described as generally fan-shaped or trapezoidally-shaped. The front end surfaces (or, in terms of the orientation of FIG. 6A, proximal end surfaces) as well as the rear end surfaces (or, in terms of the orientation of FIG. 6A, distal end surfaces) that form partial boundaries of the apertures in masks 608 and 610 can be substantially circular arc-segments, respectively, where the front end arc represents a smaller arc-segment than the rear end arc. As such, the apertures in masks 608 & 610 can be described as annular segments. As an alternative, the front end and/or the rear end can be configured as substantially planar surfaces, or some of other shape.

The formation of alternating high-Z layers 420 and low-Z layers on each structural substrate 606-i proceeds similarly to what has been described regarding FIGS. 4A-4C, and so a discussion of similarities will not be repeated for brevity.

Arrangement 400 of FIGS. 4A-4C can be described as forming layers of material that exhibit a more arcuately-uniform deposition, vis-à-vis the arcuate character reflected by front end surfaces 412F & 414F and rear end surfaces 412R & 414R, than arrangement 600 of FIG. 6. On the other hand, arrangement 600 can be described as forming layers of material that exhibit a more horizontally-uniform deposition than arrangement 400.

Tapered reflection-layer reflectors, e.g., reflector 332-i, can be incorporated into narrow band x-ray filters such as are disclosed in the copending '305 application and in the copending '927 application, respectively. A discussion of such filters follows.

Figure 7A:
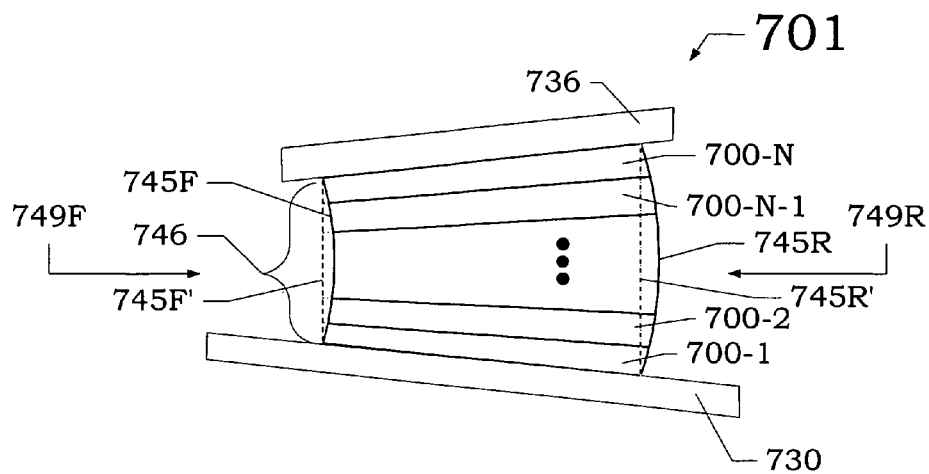
FIG. 7A is a cross-section (taken along a section line VIIA-VIIA" of FIG. 7B) of a narrow band x-ray filter, according to an embodiment of the present invention.
Figure 7B:
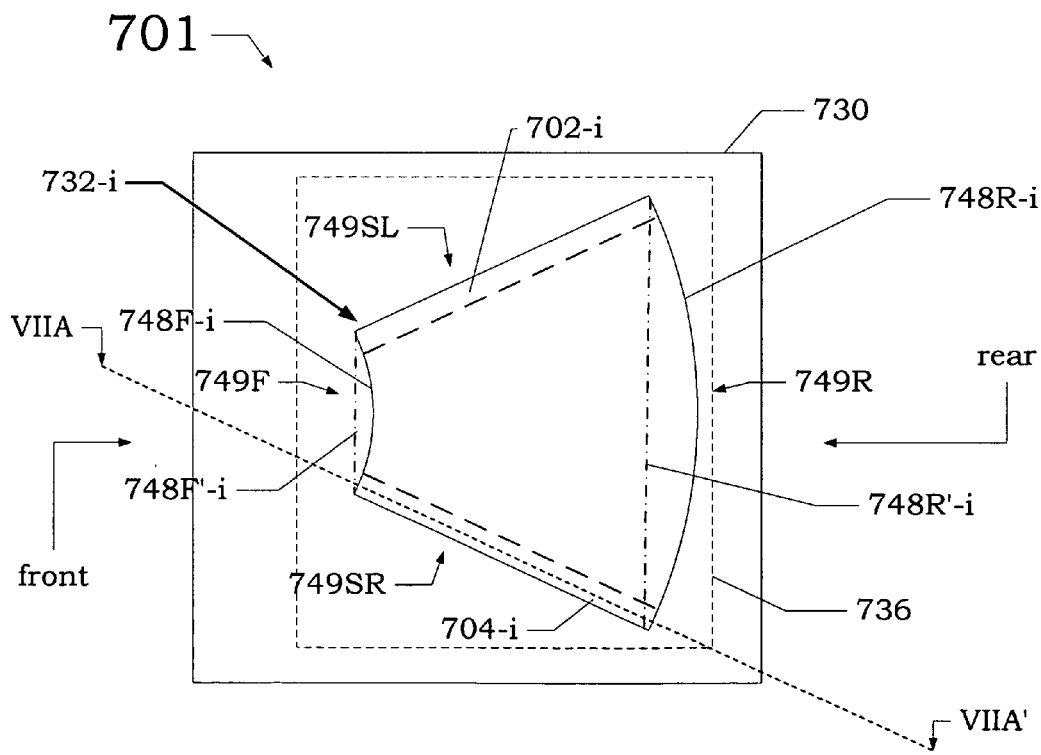
FIG. 7B is a top view of the narrow band x-ray filter of FIG. 7A.

FIG. 7A is a cross-section (taken along a section line VIIA-VIIA" of FIG. 7B) of a narrow band x-ray filter 701, according to an embodiment of the present invention. FIG. 7B is a top view of filter 701.

In FIG. 7A, a sheaf 746 of tapered reflection layer reflectors (not shown in FIG. 7A but, e.g., reflector 332-i) is depicted as disposed between a top member 736 and a base 730. More particularly, a first rack 700-1 for holding a reflector 332-i (again, not shown in FIG. 7A) is disposed on base 730. A second rack 700-2 for holding a reflector 332-i (again, not shown in FIG. 7A) is disposed on the first rack 700-1. Such a stacking of racks 700-i is continued until a rack 700-N for holding a reflector 332-i (again, not shown in FIG. 7A) is disposed upon a rack 700-N-1. Then top member 736 is disposed on rack 700-N. Details of such racks (a type of spacing structure/body) can be found in the copending '305 application.

Overall, the side silhouette of sheaf 746 (as viewed from front 749F to rear 749R in FIG. 7A) is fan-shaped or trapezoidally-shaped (with the smaller end of the trapezoid corresponding to front 749F and the bigger end corresponding to rear 749R). Also, the side silhouette of each rack 700-i can be trapezoidally-shaped in a similar manner to the silhouette of sheaf 746, although the taper of each rack 700-i can be not so great as the taper of sheaf 746. In other words, the upper and lower surfaces of rack 700-i are less divergent than the upper and lower surfaces of sheaf 746. In contrast, base 730 and top member 736 can have parallel, or substantially parallel, upper and lower surfaces.

The silhouette of reflector 732-i in 7B (again, a top view) also is generally fan-shaped or trapezoidally-shaped (again, with the smaller end of the trapezoid being located near a front end 749F of rack 700-i). More particularly, the top silhouette of reflector 732-i in FIG. 7A can be described as an annular segment. As seen in FIG. 7B, a front surface 748F-i and a rear surface 748R-i of reflector 732-i can be substantially circular arc-segments, respectively, where front surface 748F-i represents a smaller arc-segment than back surface 748R-i. As an alternative, front surface 748F-i and back surface 748F-i can be configured as substantially planar surfaces, which is indicated by dashed straight lines 748F'-i and 748R'-i, respectively.

Returning to the overall trapezoidal side silhouette of sheaf 746 in FIG. 7A, a front surface 745F and a rear surface 745R can be substantially circular arc-segments, respectively, where front surface 745F represents a smaller arc-segment than rear surface 745R. Arcuate front surface 745F can facilitate a more uniform length lfi (see FIG. 3A) between a front edge of reflector 332-i (again, not shown in FIG. 7A) and source 356. As length lli (again, see FIG. 3A) of each reflector 332-i can be substantially the same, arcuate rear surface 745R can be the consequential result of an implementation that locates front ends of reflectors 332-i so as to achieve arcuate front surface 745F. As an alternative, the front surface and rear surface of the trapezoidal silhouette can be configured as substantially planar surfaces, which is indicated by dashed straight lines 745F' and 745R', respectively.

Figure 8:
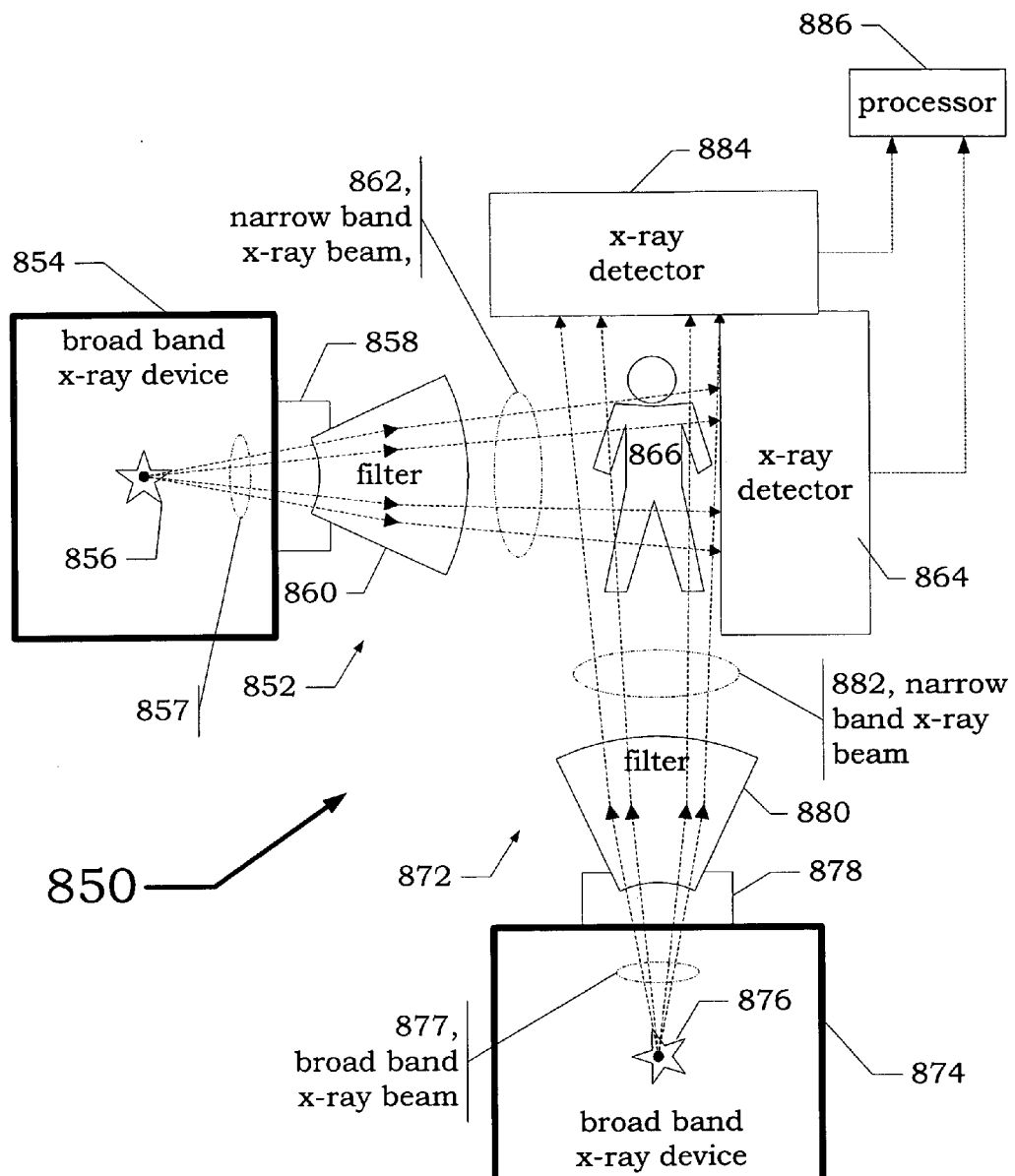
FIG. 8 is a block diagram of an x-ray radiographic system, according to an embodiment of the present invention.

FIG. 8 is a block diagram of an x-ray radiographic system 850 according to an embodiment of the present invention. System 850 can include a narrow band x-ray filter such as filter 332-i.

In FIG. 8, system 850 includes: a source 854 of a broad band beam 857 of x-rays that itself includes an anode 856 from which the broad band x-ray beam 857 is emitted; a narrow band x-ray filter 860; a focal adjustment mechanism 858; and an x-ray detector 864. Filter 860 can correspond, e.g., to filter 201. Filter 860 can be, e.g., unispectral narrow band x-ray filter 701, or one of the narrow band filters disclosed in the copending '04,the copending '927 application, etc. Alternatively, filter 860 can correspond to multi-spectral filter 1009, etc.

As used herein, the term "narrow band x-ray beam" is to be understood as at least a quasi-mono-energetic, spatially extended beam of x-rays, if not a substantially mono-energetic beam of x-rays.

Construction of focal adjustment mechanism 858 is discussed below. Source 854 and detector 864 are known in the radiographic imaging art. For example, source 854 can be the x-ray emitting portion of a known x-ray radiology device. Similarly, for example, detector 864 can be either a known type of x-ray film, a known image plate (also referred to as a storage phosphor plate, etc.) or a known x-ray detector, e.g., a solid state detector that produces an electrical output representing intensities of impinging x-rays that it receives. In the latter case of a CCD, a processor 886 would be included to harvest and process data from CCD 864 in a known manner to form an x-ray image.

Passage of broad band beam 857 through narrow band filter 860 produces a narrow band beam 862 of x-rays. Relative to anode 856, focal adjustment mechanism 858 moves filter 860 in at least one degree, and up to three degrees, of freedom. Focal adjustment mechanism 858 can be constructed, and can operate, very similarly to a lens of a camera. In a camera, the optical elements are adjusted (either manually or via one or more motors) in typically one dimension to move the focal point of the lens (via movement of the lens) onto a photographic film surface or the surface of a solid-state imager that (relative to the movable lens) has a fixed position in space. In system 850, focal adjustment mechanism 858 can be used to precisely align a focal point of filter 860 onto anode 856 in 1-3 dimensions. In other words, anode 856 can have a fixed location in space relative to filter 860, which is movable via focal adjustment mechanism 858. Alternatively, focal adjustment mechanism 858 can move filter 860 whereas anode 856 can have a relatively fixed position, etc.

In FIG. 8, a subject 866 of the x-ray radiology, e.g., a living organism such as a person, is interposed between filter 860 and detector 864 so that narrow band x-ray beam 862 impinges on subject 866. Varying attenuation of narrow band x-ray beam 862 by different parts of subject 866 casts an x-ray shadow of varying intensities onto detector 864, which detector 864 converts, e.g., into electrical signals representing an image of subject 866. In other words, detector 864 can be described as being disposed in beam 862 albeit downstream from subject 866. Alternatively, subject 866 can be some other genus and species of living organism, or an inanimate object, e.g., a package, a piece of luggage, etc.

The x-rays, in FIG. 8, that comprise narrow band beam 862 diverge away from filter 860. Such divergence causes a shadow cast by subject 866 to be magnified. To reduce such magnification (and therefore improve the accuracy of the resulting image), subject 866 should be positioned as closely to detector 864 as possible.

In FIG. 8, item nos. 854-864 and 886 can be considered a subsystem 852. A variation of system 850 can include an optional second subsystem 872 that corresponds to subsystem 852 and has optional similar components 874-884, respectively. Subsystem 872 is arranged orthogonally to subsystem 852, which can reduce or eliminate the need to change the position of the subject 866 otherwise associated with using only subsystem 352.

Figure 9:
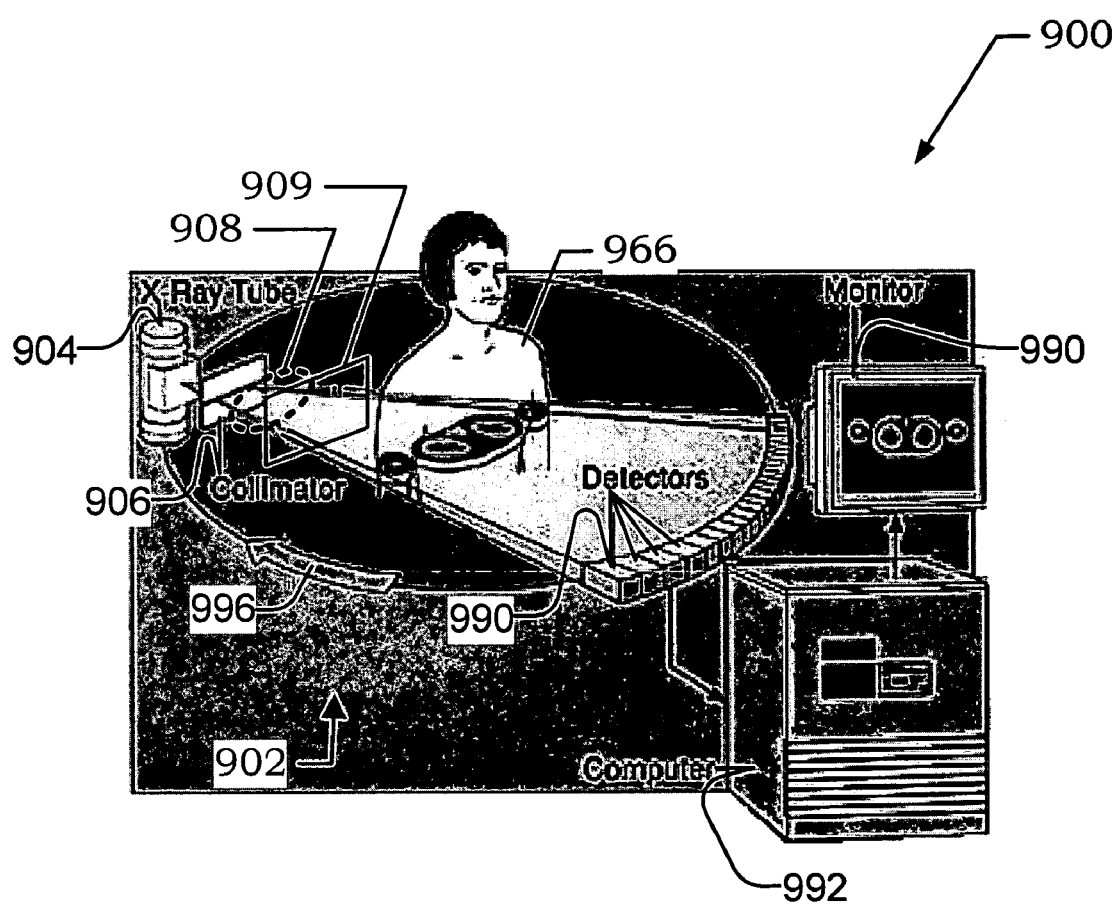
FIG. 9 is a simplified block diagram of a CT scanning system according to an embodiment of the present invention.

FIG. 9 is a simplified block diagram of another x-ray radiographic system 900, e.g., a CT scanning system, according to an embodiment of the present invention. System 900 can include a narrow band x-ray filter such as filter 332-i.

In FIG. 9, CT scanning system 900 includes a CT scanner 902, a computer 992 and a monitor 994. Included in CT scanner 902 are: a rotating gantry (not depicted for simplicity of illustration) that revolves around a subject 966; an x-ray source 904; an optional focal adjustment mechanism (not depicted for simplicity of illustration), e.g., such as focal adjustment mechanism 858; an optional collimator 906; a narrow band x-ray filter 909; and an array (e.g., an arcuate array) of x-ray detectors 990. The gantry can support x-ray source 904, the focal adjustment mechanism, collimator 906 and filter 909 and detectors 990 such that source 904, the focal adjustment mechanism, collimator 906 and filter 909 are disposed on substantially opposite sides of subject 966 as are detectors 990. Filter 909 can be, e.g., narrow band x-ray filter 701, or one of the narrow band filters disclosed in the copending '04,the copending '927 application, etc.

In the radiation imaging art, a collimator is a device used to define the size and shape of a radiation beam in radiation therapy treatment machines, e.g., CT scanner 902. Typically, a collimator is constructed of large blocks of heavy metals, e.g., steel or tungsten. Some collimators can have the positions of their parts adaptively adjusted in order to establish a desired size of a rectangular aperture into which a portion of an unshaped x-ray beam impinges.

A broad band x-ray beam is emitted from source 904 and is formed into a fan-shaped beam 908 by collimator 906. The gantry (and with it source 904, the focal adjustment mechanism, collimator 906, filter 909 and detectors 990) can be incrementally revolved around (see rotational direction indicated by reference number 996) a given axial position on subject 966. Alternatively, source 904, the focal adjustment mechanism, collimator 906 and filter 909 can remain in a substantially fixed position and the monochromatic x-ray beam output by filter 909 can be aimed at and bounced off a reflector (not shown) that is revolved around subject 966.

After completing a revolution about an axial position N, subject 966 is moved so that beam 908 would impinge upon subject 196 at a different axial position N+1. Then, the gantry is again revolved about subject 966 to collect profiles for position N+1.

For a given revolution around a given axial position on subject 966, detectors 990 can record, e.g., about 1,000 profiles (again, one-dimensional images) of the subject-attenuated x-ray beams. These profiles can be assembled by computer 992 into a two-dimensional composite image of the section that was scanned. Such two-dimensional images that have been generated for a plurality of axial positions represent subject 966 in a manner analogous to viewing the interior of a loaf of bread by cutting the bread into thin slices.

Alternatively, system 900 can be implemented such that the detectors 990 are substantially fixed in location relative to patient 966. The gantry can be arranged to move x-ray source 904, the focal adjustment mechanism, collimator 906 and filter 909 in a type of pendulum motion past patient 966. Such a scanning motion is similar to the type of scanning implemented in mammography-type devices according to the Background Art.

Further in the alternative, system 900 can be implemented as a spiral (helical) CT system (not depicted). It is noted that spiral (helical) CT scanning takes its name from the shape of the path traced out by the x-ray beam during scanning. The axial position on subject 966 at which the narrow band x-ray beam impinges can be changed at a substantially constant rate by moving subject 966 past the gantry at the substantially constant rate. Meanwhile, the gantry can be substantially continuously revolved around subject 966. In effect, a spiral path can be traced through subject 966. This spiral path results in the generation of substantially continuous data with substantially no gaps between images.

Figure 10:
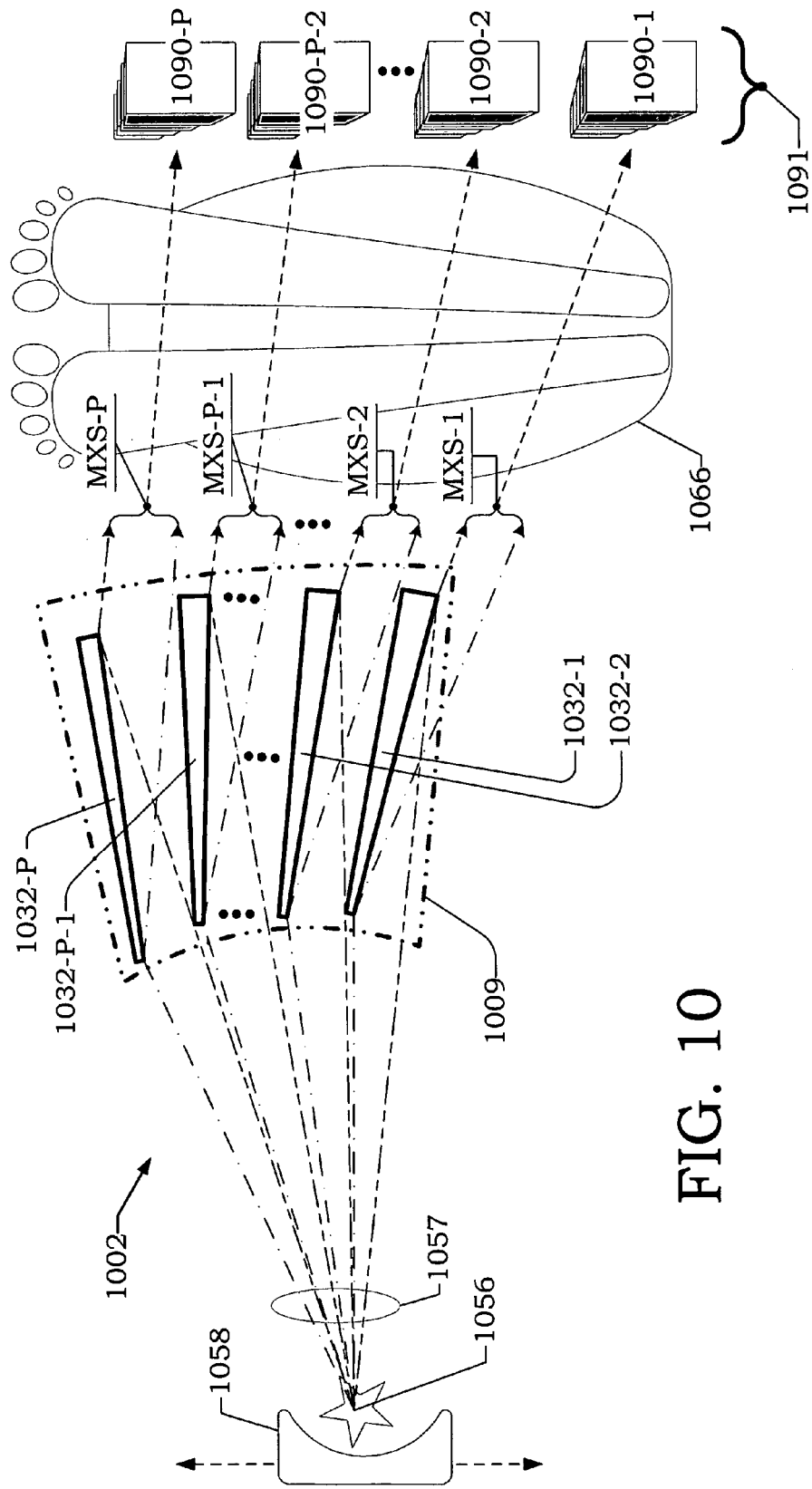
FIG. 10 is a simplified block diagram of a multispectral CT scanner according to another embodiment of the present invention.
Figure 11:
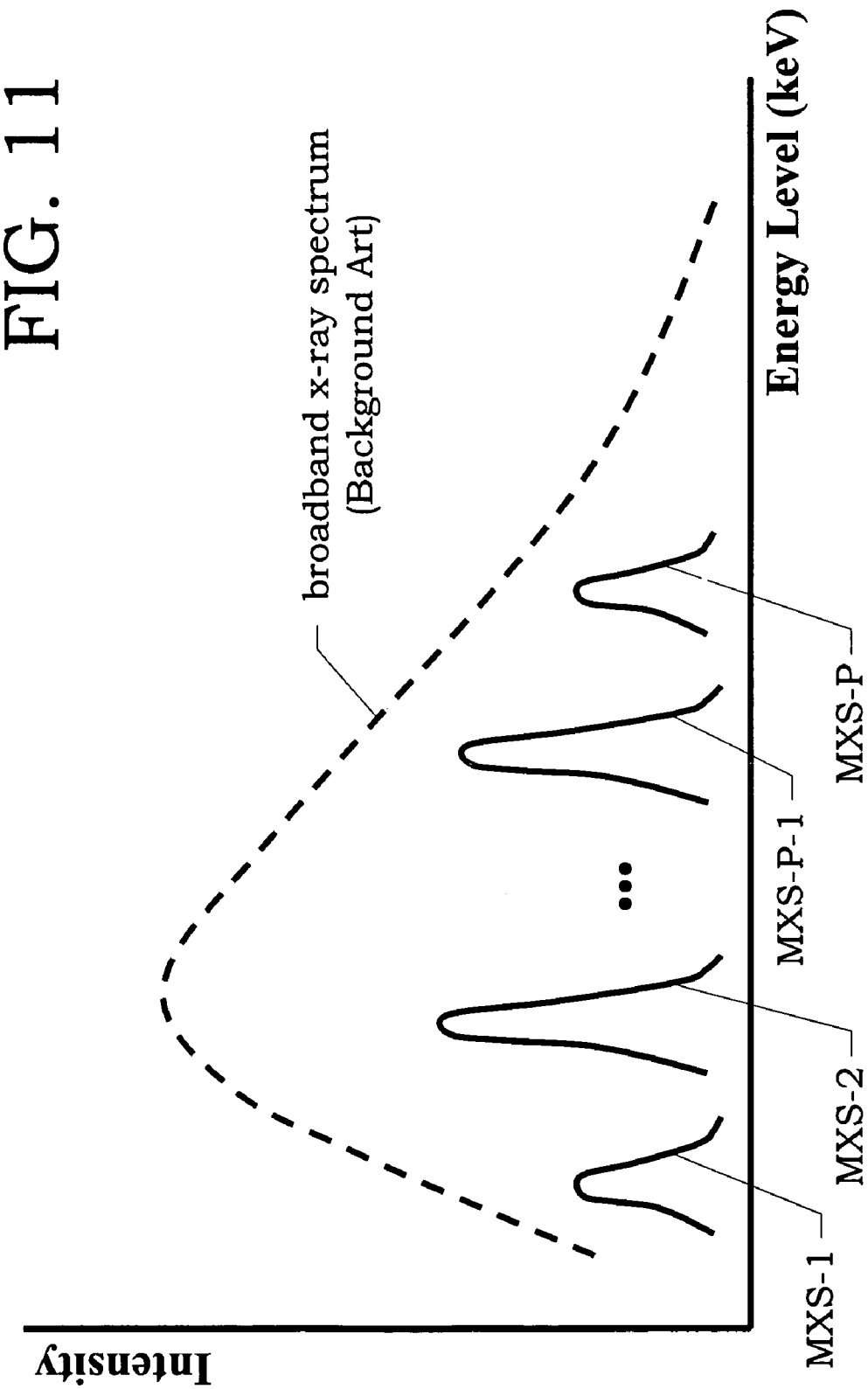
FIG. 11 is a plot of a multiple narrow bandwidth substantially monochromatic x-ray spectrums, according to an embodiment of the present invention, as well as (for contrast) a broad band beam of x-rays according to the Background Art.

FIG. 10 is a simplified block diagram of a multispectral CT scanner 1002 according to another embodiment of the present invention. FIG. 11 is a plot of a multiple narrow bandwidth substantially monochromatic x-ray spectrums MXS-1, MXS-2, . . . , MXS-P-2 and MXS-P, respectively, according to an embodiment of the present invention, as well as (for contrast) a broad band beam of x-rays according to the Background Art.

In many respects, FIG. 10 is similar to FIG. 9. Some of the similarities will be briefly reviewed.

In FIG. 10, multispectral CT scanning system 1002 includes: a rotating gantry (not depicted) that revolves around a subject 1066; an x-ray source 1056; an optional focal adjustment mechanism 1058, e.g., similar to focal adjustment mechanism 858; an optional collimator (not shown for simplicity of illustration); a multispectral narrow bands x-ray filter 1009; and a plurality 1091 of arrays (e.g., an arcuate arrays) of x-ray detectors 1090-i. The gantry can support x-ray source 1056, focal adjustment mechanism 1058, the collimator, filter 1009 and detectors 1090-i (or, in other words, its cargo) such that source 1056, focal adjustment mechanism 1058, the collimator and filter 1009 are disposed on substantially opposite sides of subject 1066 as is plurality 1091 of detectors 1091-i.

Filter 1009 can be, e.g., similar to narrow band x-ray filter 701, or one of the narrow band filters disclosed in the copending '04,the copending '1027 application, etc., albeit with the following difference. While filter 1009 can include a sheaf of P reflectors 1032-i (where P is a non-zero, positive integer), each reflector can be configured to a substantially different monochromatic x-ray band. More particularly, each of reflectors 1032-1, 1032-P-2, . . . , 1032-P-1 and 1032-P can receive a portion of a broad band (see FIG. 11), relatively larger fan-shaped beam 1057 of x-rays and therefrom can produce relatively smaller, fan-shaped beams MXS-1, MXS-2, . . . , MXS-P-2 and MXS-P, respectively, of narrow bandwidth (or, in other words, substantially monochromatic x-ray spectrums); again, see FIG. 11. Each reflector 1032-i can correspond to reflector 332-i of FIG. 3A albeit configured to a different frequency (or, in other words, central wavelength in its respective output spectrum). As such, for any two given reflectors 1032-k and 1032-k-1 in filter 1009, at least one of the thickness of the reflecting layers at the front end of the reflector (namely tf$_k$ and tf$_{k-1}$, respectively) and the thickness of the reflecting layers at the rear end of the reflector (namely, reflector tr$_k$ and tr$_{k-1}$, respectively) differ. Again, see Equation No. (7) above. Hence, filter 1009 can be described as a multispectral narrow bands x-ray filter.

There can be P arrays (e.g., arcuate arrays) of detectors 1090-i for the P fan-shaped beams of substantially monochromatic x-rays. More particularly, array 1090-1 of detectors can be arranged to receive spectrum MSX-1, array 1090-2 of detectors can be arranged to receive spectrum MSX-2, . . . , array 1090-P-1 of detectors can be arranged to receive spectrum MSX-P-1, and array 1090-P of detectors can be arranged to receive spectrum MSX-P.

A broad band x-ray beam is emitted from source 1056 and can be shaped, e.g., into a relatively larger fan-shaped beam 1057, by the collimator. The gantry (and its cargo) can be incrementally revolved around a given axial position on subject 1066. Alternatively, source 1056, focal adjustment mechanism 1058, the collimator and filter 1009 can remain in a substantially fixed position and plurality 1091 of different monochromatic x-ray beams output by filter 1009 can be aimed at and bounced off a reflector (not shown) that is revolved around subject 1066.

Alternatively, CT scanner 1002 can be implemented such that plurality 1091 of arrays of detectors 1090-i are substantially fixed in location relative to patient 1066. The gantry can be arranged to move x-ray source 1056, focal adjustment mechanism 1058, collimator 1006 and filter 1009 in a type of pendulum motion past patient 10906. Such a scanning motion is similar to the type of scanning implemented in mammography-type devices according to the Background Art.

Further in the alternative, scanner 1002 can be implemented as a spiral (helical) CT (not depicted).

Relative to source 1056, focal adjustment mechanism 1058 moves filter 1009 in at least one degree, and up to three degrees, of freedom. In system 850, focal adjustment mechanism 858 can be used to precisely align a focal point of filter 1009 onto anode 856 in 1-3 dimensions. The same can be true of focal adjustment mechanism 1058. Further, focal adjustment mechanism 1058 can be used to slightly adjust angles α1i and α2i in order to slightly tune the central wavelengths of narrow band beams of x-rays, respectively, produced by filter 1009. As such, there can be a plurality of focal points corresponding to a plurality of central wavelengths, respectively. Movement of source 1056 can substantially uniformly shift all central wavelengths of the narrow band beams of x-rays.

It is noted that each of focal adjustment mechanisms 858, 878 and that of system 900 similarly can be used to tune the central wavelength of the narrow band beam of x-rays produced by filters 860, 880 and 909, respectively. Further in the alternative, each of sources 1056 904 can have a relatively fixed location in space, while focal adjustment mechanisms 1058 and that of system 900 can move filters 1009 and 909, etc.

Figure 12A:
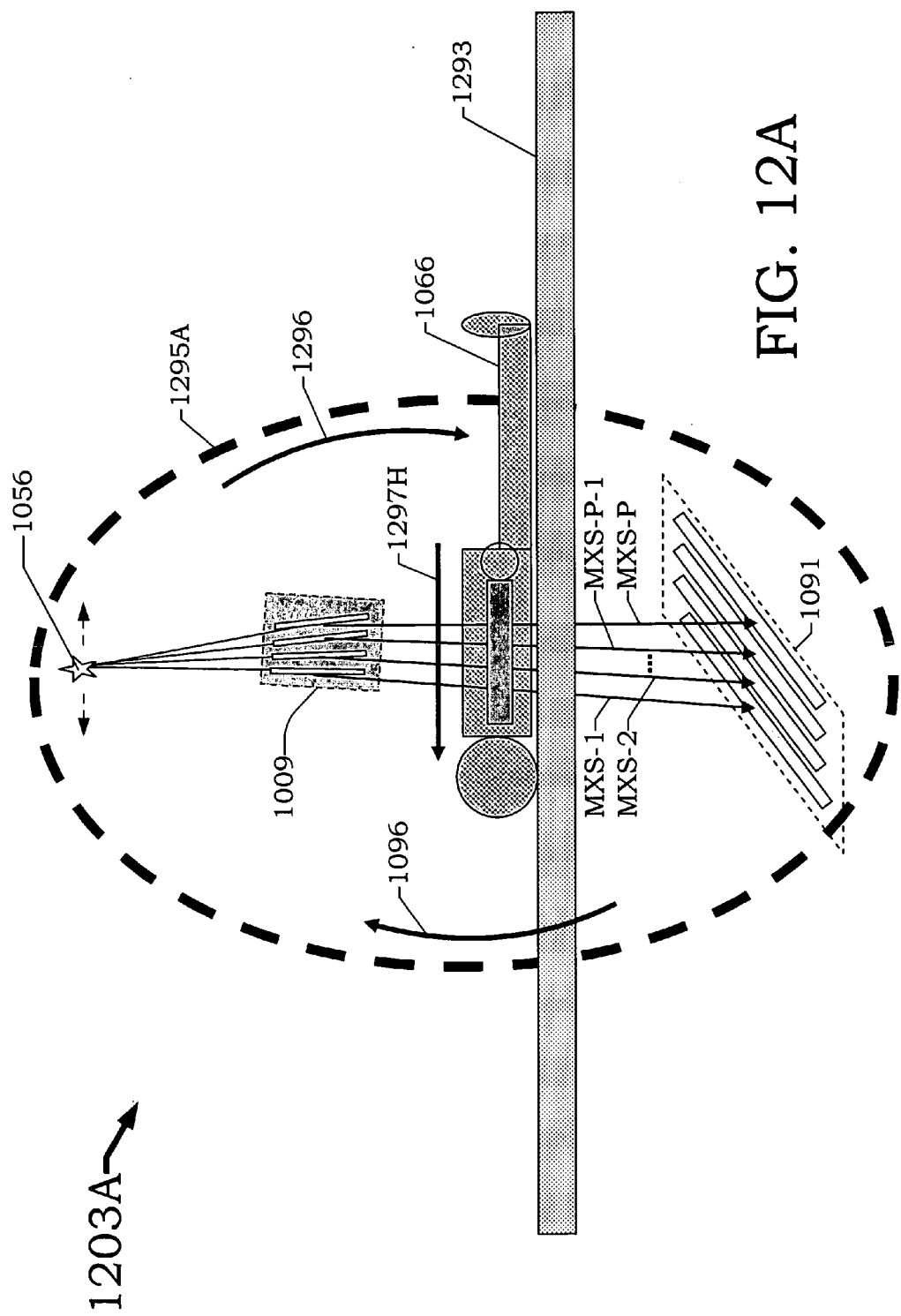
FIG. 12A is a simplified block diagram of a multispectral x-ray imaging system, according to an embodiment of the present invention.

FIG. 12A is a simplified block diagram of a multispectral x-ray imaging system 1203A according to an embodiment of the present invention. In FIG. 12A, multispectral imaging system 1203A takes the form of a CT system.

In many respects, FIG. 12A is similar to FIGS. 9 and 10. Some of the similarities will be briefly reviewed. In FIG. 12, multispectral imaging system 1203A includes: a rotating gantry 1295A that revolves around subject 1066; x-ray source 1056; a focal adjustment mechanism (not shown for simplicity of illustration), e.g., such as focal adjustment mechanism 1058; an optional collimator (not shown for simplicity of illustration); multispectral narrow bands x-ray filter 1009; and plurality 1091 of arrays (e.g., an arcuate arrays) of x-ray detectors. Gantry 1295A can support x-ray source 1056, the focal adjustment mechanism, the collimator, filter 1009 and plurality 1091 of detectors such that source 1056, the focal adjustment mechanism, the collimator and filter 1009 are disposed on substantially opposite sides of subject 1066 as is plurality 1091 of detectors.

A broad band x-ray beam is emitted from source 1056 and is formed into P fan-shaped beams of substantially monochromatic x-rays by multispectral narrow bands x-ray filter 1009. Gantry 1295A (and therewith its cargo of source 1056, the focal adjustment mechanism, the collimator, filter 1009 and plurality 1091 of detectors) can be incrementally revolved around (see rotational direction indicated by reference number 1296) a given axial position on subject 1066, where subject 1096 is disposed on a platform 1293. Alternatively, source 1056, the focal adjustment mechanism, the collimator and filter 1009 can remain in a substantially fixed position and the multispectral monochromatic x-ray beams output by filter 1009 can be aimed at and bounced off a reflector(s) (not shown) that is revolved around subject 1066.

Figure 12B:
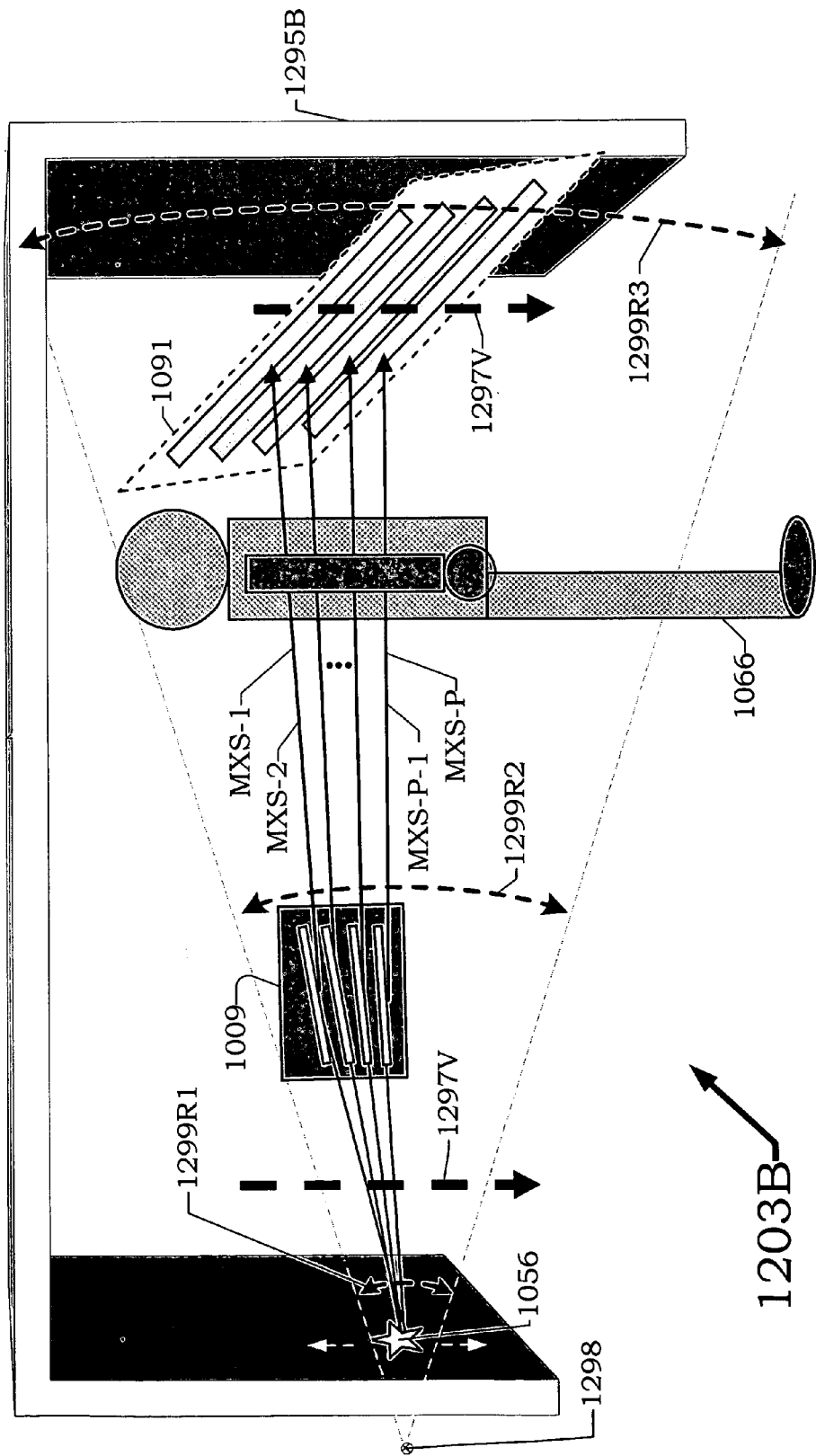
FIG. 12B is a simplified block diagram of another multispectral x-ray imaging system according to an embodiment of the present invention.

FIG. 12B is a simplified block diagram of a multispectral x-ray imaging system 1203B according to an embodiment of the present invention. In FIG. 12B, multispectral imaging system 1203B takes the form of a scanning x-ray system in which the subject moves and the imaging circuitry is stationary.

In some respects, FIG. 12B is similar to FIG. 12A. Some of the similarities will be briefly reviewed. In FIG. 12B, multispectral imaging system 1203B includes: a mobile gantry 1295B that moves substantially uni-dimensionally with respect to subject 1066; x-ray source 1056; a focal adjustment mechanism (not shown for simplicity of illustration), e.g., such as focal adjustment mechanism 1058; an optional collimator (not shown for simplicity of illustration); multispectral narrow bands x-ray filter 1009; and plurality 1091 of arrays of x-ray detectors.

A broad band x-ray beam is emitted from source 1056 and is formed into P fan-shaped beams of substantially monochromatic x-rays by multispectral narrow bands x-ray filter 1009. Source 1056, the focal adjustment mechanism, the collimator, filter 1009 and plurality 1091 of detectors can have fixed positions relative to one another.

Gantry 1295B (and its cargo) can be incrementally moved along in a direction parallel to a reference axis 1297V. Subject 1066, e.g., who can be standing on the floor, is positioned such that the multispectral narrow bands of x-rays pass through, e.g., a parallel reference axis located in subject 1066. Alternatively, gantry 1295B can be arranged to move its cargo in a type of pendulum motion, e.g., as indicated by arcuate indicators 12299R1, 1299R2 and 1299R3, about a rotational axis 1298.

Figure 12C:
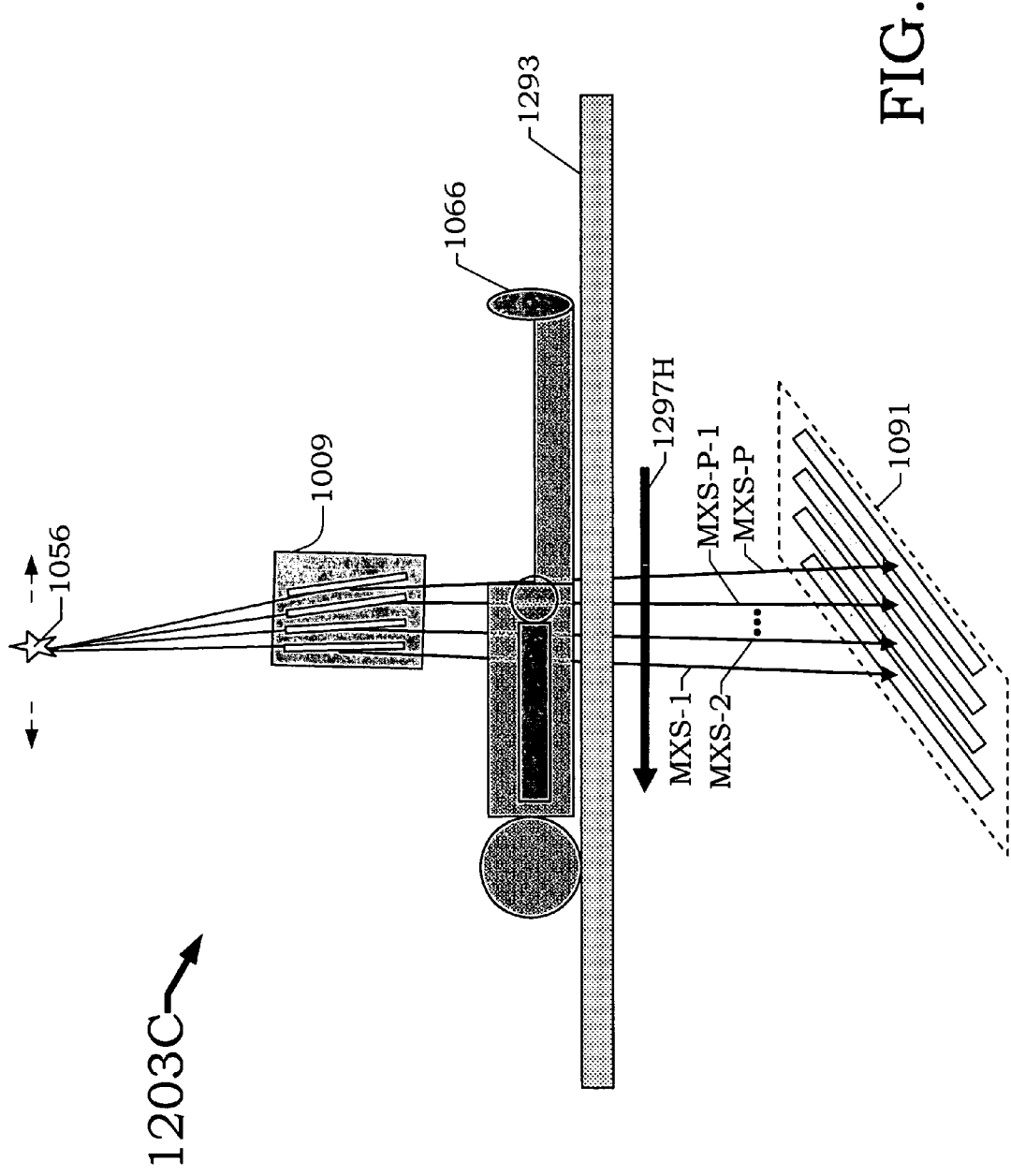
FIG. 12C is a simplified block diagram of yet another multispectral x-ray imaging system according to an embodiment of the present invention.

FIG. 12C is a simplified block diagram of a multispectral x-ray imaging system 1203C according to an embodiment of the present invention. In FIG. 12C, multispectral imaging system 1203C takes the form of a scanning x-ray system in which the subject is stationary and the imaging circuitry moves.

In some respects, FIG. 12C is similar to FIG. 12B, and also FIG. 12A. Some of the similarities will be briefly reviewed. In FIG. 12C, multispectral imaging system 1203C includes: an x-ray source 1056; a focal adjustment mechanism (not shown for simplicity of illustration), e.g., such as focal adjustment mechanism 1058; an optional collimator (not shown for simplicity of illustration); multispectral narrow bands x-ray filter 1009; and plurality 1091 of arrays of x-ray detectors.

A broad band x-ray beam is emitted from source 1056 and is formed into P fan-shaped beams of substantially monochromatic x-rays by multispectral narrow bands x-ray filter 1009. Source 1056, the focal adjustment mechanism, the collimator, filter 1009 and plurality 1091 of detectors can have fixed positions relative to one another. Subject 1066 can be incrementally moved, via platform 1293, past an axial reference position lying on a reference axis 1297H. Alternatively, and similarly to system 1203B, gantry 1295C can be arranged to move its cargo in a type of pendulum motion.

The examples of multispectral x-radiographic devices and systems noted above have been described in terms of reflectors each of which has tapered coatings such as in reflector 332-i. Alternatively, one or more (or even all) reflectors in such a multispectral device or system could include substantially non-tapered coatings, such as in the '305 application and in the copending '927 application. While such non-tapered coatings would produce a less narrow band of x-rays, respectively, the alternative device nonetheless would exhibit multiple narrow bands of x-rays.

As another alternative, a unispectral x-radiographic device and system such as has been noted above can be operated to achieve multispectral imaging, e.g., if provided with a focal adjustment mechanism (e.g., such as is discussed above). For example, a first image of the subject can be made using a first central wavelength for the unispectral narrow band beam of x-rays. Afterward, the focal adjustment mechanism can be manipulated to change the unispectral narrow band beam of x-rays so that it exhibits a second central wavelength different from the first central wavelength. Then a second image of the subject can be made. Such a wavelength tuning & re-imaging process can be repeated as needed. Though representing a lengthier overall process than is associated with a multispectral x-radiographic device or system, such operation of the unispectral x-radiographic device or system nevertheless can achieve multispectral imaging.

Embodiments of the present invention having been thus described, it will be obvious that the same may be varied in many ways. Such variations are not to be regarded as a departure from the spirit and scope of the present invention, and all such modifications are intended to be included within the scope of the present invention.

What is claimed is:

1. An x-ray reflector comprising:
   a substrate;
   a first layer formed on the substrate, the first layer including a relatively higher-Z material, where Z represents the atomic number; and
   a second layer formed on the first layer, the second layer including a relatively lower-Z material;
   both of the first layer and the second layer exhibiting a taper along an axis extending between a first end of the substrate and a second end of the substrate, at least one of the first layer and the second layer also substantially exhibiting arcuate uniformity along a ciiven arc defined by a radius extending from a reference point on the axis; and
   wherein, at any given axial position along the axial direction and treating the first and second layers as together representing a bi-layer structure, a thickness of the first layer represents about ⅖ of a total thickness of the bi-layer structure, and a thickness of the second layer represents about ⅗ of the total thickness of the bi-layer structure.

2. The x-ray reflector of claim 1, wherein the taper is non-linear.

3. The x-ray reflector of claim 2, wherein the taper is described by the following relation, $$\frac{t_{axp1}}{t_{axp2}} \approx \frac{\sin\alpha 1}{\sin\alpha 2}$$

where $t_{axp1}$ represents a combined thickness of the first and second layers at a first axial position along the axial direction, α1 represents an incidence angle of x-rays from a source thereof that impinge upon the respective layer at the first axial $t_{axp2}$ represents a combined thickness of the first and second layers at a second axial position along the axial direction farther from the source than the first axial position, and α2 represents an incidence angle of x-rays from the source that impinge upon the respective layer at the second axial position.

4. The x-ray reflector of claim 1, wherein:
   the first and second layers together represent a bi-layer structure; and
   the x-ray reflector further includes a plurality of the bi-layer structures stacked successively upon each other.

5. A method of making a narrow band x-ray filter, the method comprising;
   providing a base;
   providing one or more x-ray reflectors, each reflector having at least one bi-layer structure that includes a relatively higher-Z material and a relatively lower-Z material, the bi-layer structure exhibiting a taper along an axis, the bi-layer structure also substantially exhibiting arcuate uniformity along a given arc defined by a radius extending from a reference point on the axis; and
   stacking the one or more reflectors upon the substrate;
   wherein the step of stacking, for each reflector, includes the following,
      disposing a set of one or more spacing bodies on a respective underlying structure, and
      disposing the reflector on the set of one or more spacing bodies.

6. The method of claim 5, further comprising:
   mechanically connecting the one or more successively-stacked units to the substrate so as to form a sheaf of reflectors.

7. A filter of to produce one or more narrow band beams of x-rays, the filter comprising:
   a base;
   a sheaf of one or more x-ray reflectors stacked upon each other, the sheaf being disposed upon the base, each reflector having at least one bi-layer structure that includes a relatively higher-Z material and a relatively lower-Z material, the bi-layer structure exhibiting a taper along an axis, the bi-layer structure also substantially exhibiting arcuate uniformity along a given arc defined by a radius extending from a reference point on the axis; and a set of one or more spacing bodies to support each of the one or more x-ray reflectors, respectively;

each set of one or more spacing bodies being interposed between a respective underlying structure and a respective reflector.

8. A filter to produce one or more narrow band beams of x-rays, the filter comprising:

a base; and a sheaf of one or more x-ray reflectors stacked upon each other, the sheaf being disposed upon the base, each reflector having at least one bi-layer structure that includes a relatively higher-Z material and a relatively lower-Z material, the bi-layer structure exhibiting a taper along an axis, the bi-layer structure also substantially exhibiting arcuate uniformity along a given arc defined by a radius extending from a reference point on the axis;

wherein the sheaf includes at least a first and a second one of the x-ray reflectors stacked upon each other; and wherein a taper of the at least one bi-layer structure in the first reflector differs from a taper of the at least one bi-layer structure in the second reflector such that the first reflector is configured to produce a different narrow band of x-rays than the second reflector.

9. An apparatus to produce one or more narrow band beams of x-rays, the apparatus comprising:

a source of a first x-ray beam;

a multispectral narrow bands x-ray filter having a first end, a second end and one or more focal points located nearer to the first end than to the second end, the filter including at least one reflector of x-rays, each reflector having at least one bi-layer structure that includes a relatively higher-Z material and a relatively lower-Z material, the bi-layer structure exhibiting a taper along an axis, the bi-layer structure also substantially exhibiting arcuate uniformity along a given arc defined by a radius extending from a reference point on the axis;

the source being disposed substantially at an instance of the one or more focal points such that at least two narrow band beams of x-rays emanate from the second end of the filter;

the filter including at least first and second reflectors; and a taper of the at least one bi-layer structure in the first reflector differing from a taper of the at least one bi-layer structure in the second reflector such that the first reflector is configured to produce a different narrow band of x-rays than the second reflector.

10. The apparatus of claim 9, wherein:

at least one of the source and the filter is movable in at least one dimension; and the apparatus further comprises a focal adjustment mechanism operable to move at least one of the source and filter in the at least one dimension and thus tune center wavelengths of the at least two narrow band beams of x-rays, respectively.

11. An x-ray imaging device comprising:

the apparatus of claim 9, an arrangement of x-ray detectors; and a gantry to hold at least the source, filter and detectors;

wherein the gantry is operable to move the source, filter and detectors in at least two dimensions with respect to a subject that is to be imaged.

12. The apparatus of claim 11, further comprising:

a movable platform operable to move the subject relative to one of a position of and motion of the gantry.

13. The apparatus of claim 11, wherein the gantry is arranged to move at least the source, filter and detectors in a type of one of a circular, helical, linear and pendulum type of motion relative to one of a position of and motion of the subject.

14. A method of using x-rays to produce an image of a subject, the method comprising:

providing an x-ray filter including one or more x-ray reflectors, each reflector having at least one bi-layer structure that includes a relatively higher-Z material and a relatively lower-Z material, the bi-layer structure exhibiting a taper in an axial direction along an axis;

producing at least two narrow band beams of x-rays using the x-ray filter;

disposing a subject in the at least two narrow band beams; and disposing at least one array of x-ray detectors in the at least two narrow band beams downstream from the subject;

wherein the step of producing includes the following, providing a narrow band x-ray filter, configuring a source of a broad band beam of x-rays at a first focal length of the filter so as to achieve a first central wavelength of a resulting narrow band of x-rays, reconfiguring, after initial occurrences of the steps of disposing the subject and disposing the at least one array of x-ray detectors, a source of a broad band beam of x-rays at a second focal length of the filter so as to achieve a second central wavelength different than the first central wavelength, and repeating the steps of disposing the subject and disposing the at least one array of x-ray detectors.

15. The method of claim 14, wherein the step of producing generates the at least two narrow band beams of x-rays substantially concurrently.

16. An apparatus to produce at least two narrow band beams of x-rays having different center wavelengths, respectively, the apparatus comprising:

a source of a relatively broad band beam of x-rays; and an x-ray filter operable to produce one or more narrow band beams of x-rays, the filter having a first end, a second end and one or more focal points located nearer to the first end than to the second end;

the source being disposed substantially at an instance of the one or more focal points such that one or more narrow band beams of x-rays emanate from the second end of the filter;

at least one of the following being true, the filter being arranged with respect to the source to produce susbstantially concurrently according to a single arrangement at least two narrow band beams of x-rays having different center wavelengths, respectively, and the filter and the source being adaptively arrangible into at least two arrangements with respect to the source to produce the at least two narrow band beams of x-rays.

17. The apparatus of claim 16, wherein:

the filter is a multispectral narrow bands type of x-ray filter that includes at least first and second reflectors, each reflector having at least one bi-layer structure that includes a relatively higher-Z material and a relatively lower-Z material, the bi-layer structure exhibiting a taper in an axial direction; and a taper of the at least one bi-layer structure in the first reflector differs from a taper of the at least one bi-layer structure in the second reflector such that the first reflector is configured to produce a different narrow band of x-rays than the second reflector.

18. The apparatus of claim 17, wherein:
at least one of the source and the filter is movable in at least one dimension; and
the apparatus further comprises a focal adjustment mechanism operable to move at least one of the source and filter in the at least one dimension and thus tune center wavelengths of the at least two narrow band beams of x-rays, respectively.

19. The apparatus of claim 16, wherein:
the filter is a unispectral type of x-ray filter operable to produce one narrow band beam of x-rays;
at least one of the source and the filter is movable in at least one dimension such that the adaptive arrangibility of the filter and the source includes the following,
a first arrangement in which the source is disposed at a first focal length of the filter so as to achieve a first central wavelength of a resulting narrow band of x-rays, and
a second arrangement in which the source is disposed at a second focal length of the filter so as to achieve a second central wavelength of a resulting narrow band of x-rays; and
the apparatus further comprises a focal adjustment mechanism operable to move at least one of the source and filter in the at least one dimension so as to selectively adopt one of the first arrangement and the second arrangement and thus tune a center wavelength of the one narrow band beam of x-rays.

20. An x-ray imaging device comprising:
the apparatus of claim 16;
an arrangement of x-ray detectors; and
a gantry to hold at least the source, filter and detectors;
wherein the gantry is operable to move the source, filter and detectors in at least two dimensions with respect to a subject that is to be imaged.

21. A method of producing at least two narrow band beams of x-rays, the method comprising:
providing a source of a relatively broad band beam of x-rays;
providing an x-ray filter operable to produce one narrow band beam of x-rays, the filter having a first end, a second end and one or more focal points located nearer to the first end than to the second end;
disposing the source substantially at a first instance of the one or more focal points of the filter so as to achieve a first central wavelength of a resulting first narrow band beam of x-rays; and
disposing the source substantially at a second instance of the one or more focal points of the filter so as to achieve a second central wavelength of a resulting second narrow band beam of x-rays.

22. The method of claim 21, wherein the step of disposing the source at the second instance of the one or more focal points includes:
moving at least one of the source and filter in at least one dimension to change an output of the filter from exhibiting the first central wavelength to exhibiting the second central wavelength.

23. A method of using x-rays to produce an image of a subject, the method comprising:
producing at least two narrow band beams of x-rays according to the method of claim 21;
disposing a subject in the at least two narrow band beams; and
disposing at least one array of x-ray detectors in the at least two narrow band beams downstream from the subject.

24. The method of claim 14, wherein the bi-layer structure also substantially exhibits arcuate uniformity along a given arc defined by a radius extending from a reference point on the axis.

25. The x-ray reflector of claim 1, wherein an interface between the first layer and the second layer is substantially planar.

26. The method of claim 5, wherein, for each of the at least one bi-layer structure, an interface between the relatively higher-Z material and the relatively lower-Z material is substantially planar.

27. The filter of claim 7, wherein, for each of the at least one bi-layer structure, an interface between the relatively higher-Z material and the relatively lower-Z material is substantially planar.

28. The apparatus of claim 9, wherein, for each of the at least one bi-layer structure, an interface between the relatively higher-Z material and the relatively lower-Z material is substantially planar.

29. The filter of claim 8, wherein, for each of the at least one bi-layer structure, an interface between the relatively higher-Z material and the relatively lower-Z material is substantially planar.

* * * * *